United States Patent
Isobe et al.

(10) Patent No.: US 9,126,339 B2
(45) Date of Patent: *Sep. 8, 2015

(54) REMOTE CONTROLLED ACTUATOR ASSEMBLY

(75) Inventors: Hiroshi Isobe, Iwata (JP); Yoshitaka Nagano, Iwata (JP)

(73) Assignee: NTN CORPORATION, Osaka (JP)

( * ) Notice: Subject to any disclaimer, the term of this patent is extended or adjusted under 35 U.S.C. 154(b) by 114 days.

This patent is subject to a terminal disclaimer.

(21) Appl. No.: 13/824,741

(22) PCT Filed: Sep. 21, 2011

(86) PCT No.: PCT/JP2011/071449
§ 371 (c)(1),
(2), (4) Date: Mar. 18, 2013

(87) PCT Pub. No.: WO2012/043324
PCT Pub. Date: Apr. 5, 2012

(65) Prior Publication Data
US 2013/0184863 A1    Jul. 18, 2013

(30) Foreign Application Priority Data
Sep. 30, 2010    (JP) .................... 2010-220972

(51) Int. Cl.
*B25J 17/00*    (2006.01)
*B25J 11/00*    (2006.01)
(Continued)

(52) U.S. Cl.
CPC ............. *B25J 11/00* (2013.01); *A61B 17/16* (2013.01); *A61B 19/2203* (2013.01);
(Continued)

(58) Field of Classification Search
CPC ........................ A61B 17/1631; B23B 45/005

USPC ............. 700/245, 253, 257, 258; 901/1, 2, 8, 901/14–20; 318/568.12, 568.15, 568.21; 173/190, 44, 39, 2; 606/1, 139, 130, 606/180, 80, 85
See application file for complete search history.

(56) References Cited

U.S. PATENT DOCUMENTS

| | | |
|---|---|---|
| 4,265,231 A | 5/1981 | Scheller, Jr. et al. |
| 4,466,429 A | 8/1984 | Loscher et al. |

(Continued)

FOREIGN PATENT DOCUMENTS

| | | |
|---|---|---|
| DE | 10 2006 030 688 A1 | 4/2008 |
| JP | 7-184929 | 7/1995 |

(Continued)

OTHER PUBLICATIONS

International Search Report mailed Oct. 25, 2011, issued in corresponding PCT Application PCT/JP2011/071449.

(Continued)

*Primary Examiner* — Dalena Tran

(57) ABSTRACT

An actuator main body mounted on an operating bench includes a main body base end housing fixed to the operating bench, an elongated spindle guide section having its base end connected with the main body base end housing, a distal end member fitted to a front end thereof for alteration in attitude, and a tool rotatably provided in the distal end member. Within the spindle guide section, a rotary shaft for transmitting a rotation of a tool rotation drive source to the tool and an attitude altering member for altering the attitude of the distal end member are provided. Within the main body base end housing, an attitude altering drive mechanism for selectively advancing or retracting the attitude altering member when driven by an attitude altering drive source is provided.

13 Claims, 27 Drawing Sheets

(51) Int. Cl.
*A61B 19/00* (2006.01)
*A61B 17/16* (2006.01)

(52) U.S. Cl.
CPC ........ *A61B 17/1631* (2013.01); *A61B 17/1668* (2013.01); *A61B 2019/2223* (2013.01); *Y10S 901/02* (2013.01); *Y10T 74/20201* (2015.01)

(56) References Cited

U.S. PATENT DOCUMENTS

| | | | |
|---|---|---|---|
| 5,769,092 A | 6/1998 | Williamson, Jr. | |
| 6,210,377 B1 * | 4/2001 | Ouchi | 604/264 |
| 7,682,357 B2 * | 3/2010 | Ghodoussi et al. | 606/1 |
| 2007/0265653 A1 | 11/2007 | Suzuki | |
| 2011/0138962 A1 | 6/2011 | Ozaki et al. | |
| 2011/0295263 A1 | 12/2011 | Nishio et al. | |
| 2011/0319912 A1 | 12/2011 | Nishio et al. | |

FOREIGN PATENT DOCUMENTS

| | | |
|---|---|---|
| JP | 2001-17446 | 1/2001 |
| JP | 2005-305585 | 11/2005 |
| JP | 2005-351379 | 12/2005 |
| JP | 2007-301149 | 11/2007 |
| JP | 2010-63876 | 3/2010 |
| JP | 2010-69289 | 4/2010 |
| JP | 2010-69290 | 4/2010 |
| WO | WO 2010/018665 A1 | 2/2010 |
| WO | WO 2010/092820 A1 | 8/2010 |
| WO | WO 2010/101086 A1 | 9/2010 |

OTHER PUBLICATIONS

International Preliminary Report on Patentability mailed Apr. 18, 2013 for corresponding International Application No. PCT/JP2011/071449.

Japanese Office Action issued Jun. 3, 2014 in corresponding Japanese Patent Application No. 2010-220972.

* cited by examiner

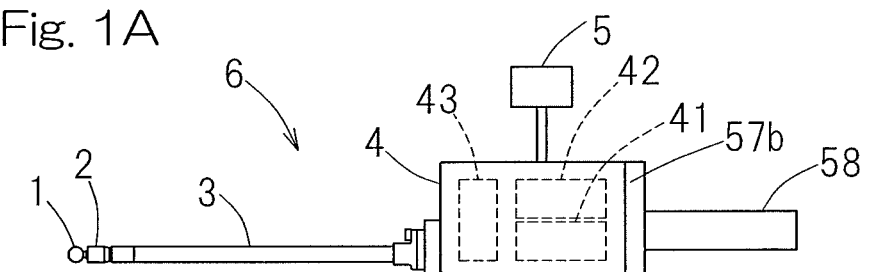
Fig. 1A
Fig. 1B
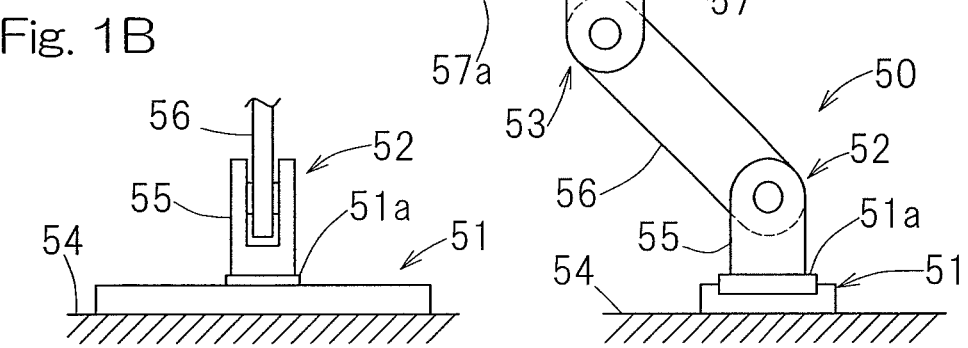
Fig. 2
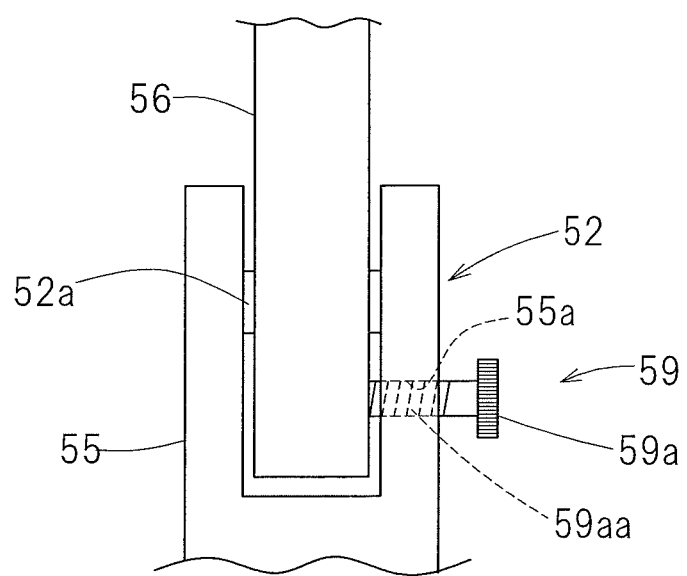

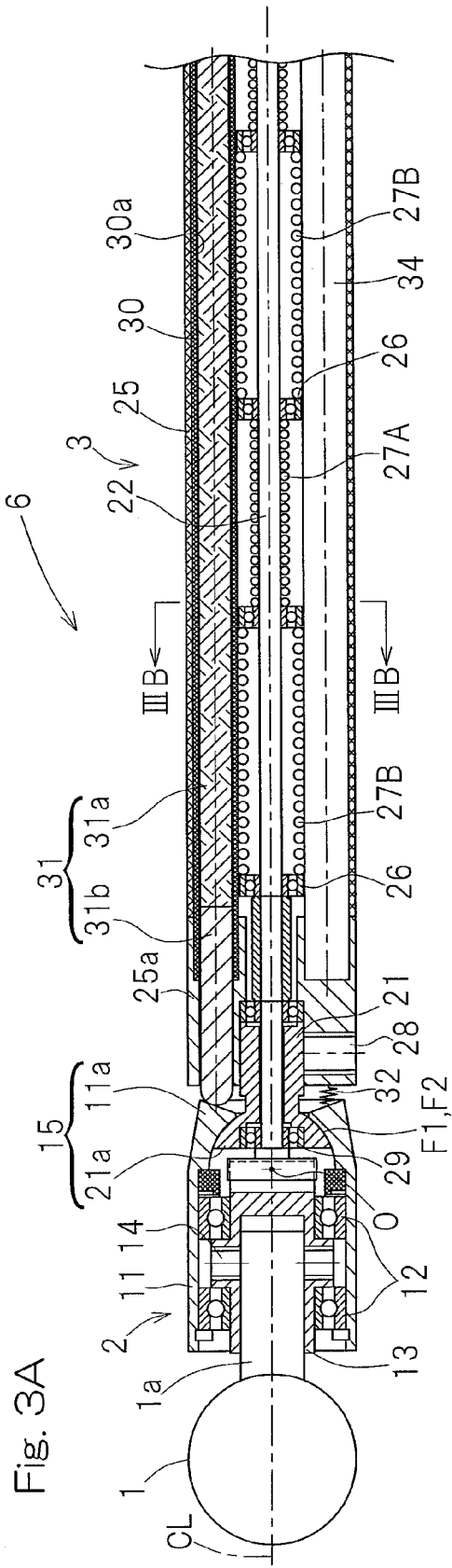
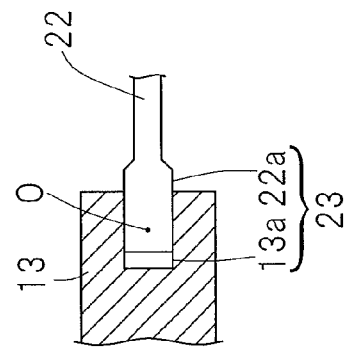
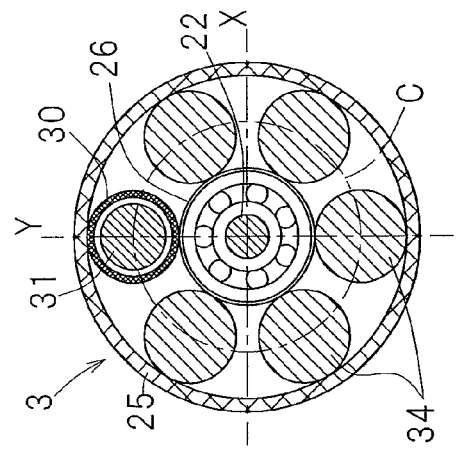
Fig. 3A
Fig. 3C
Fig. 3B

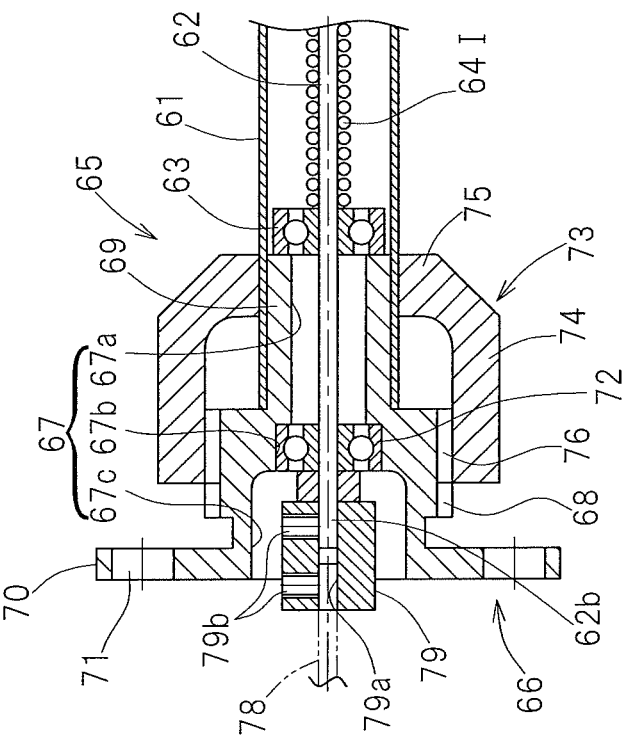

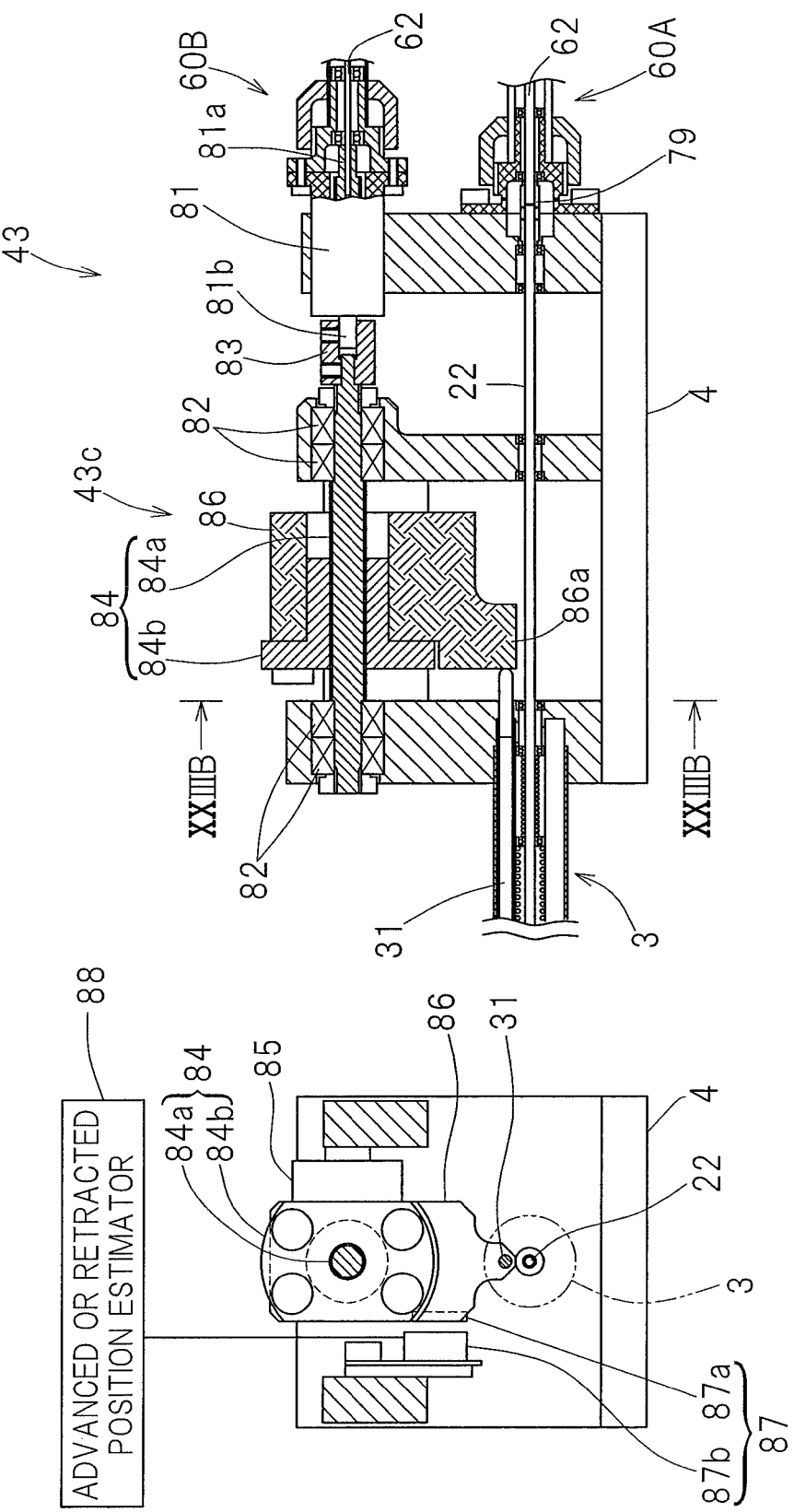

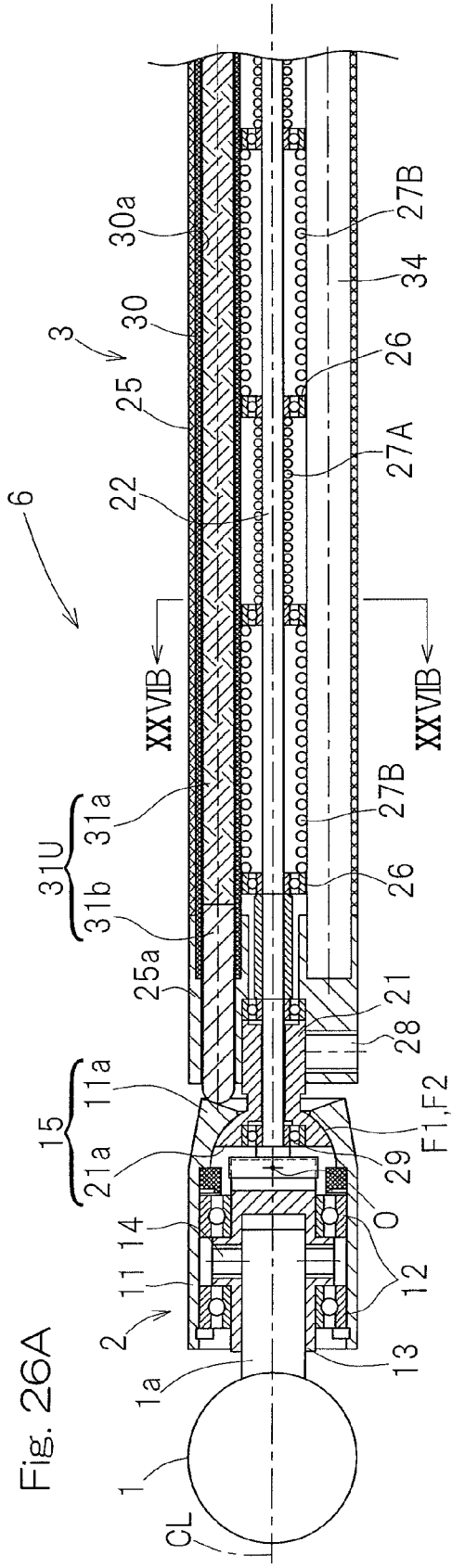

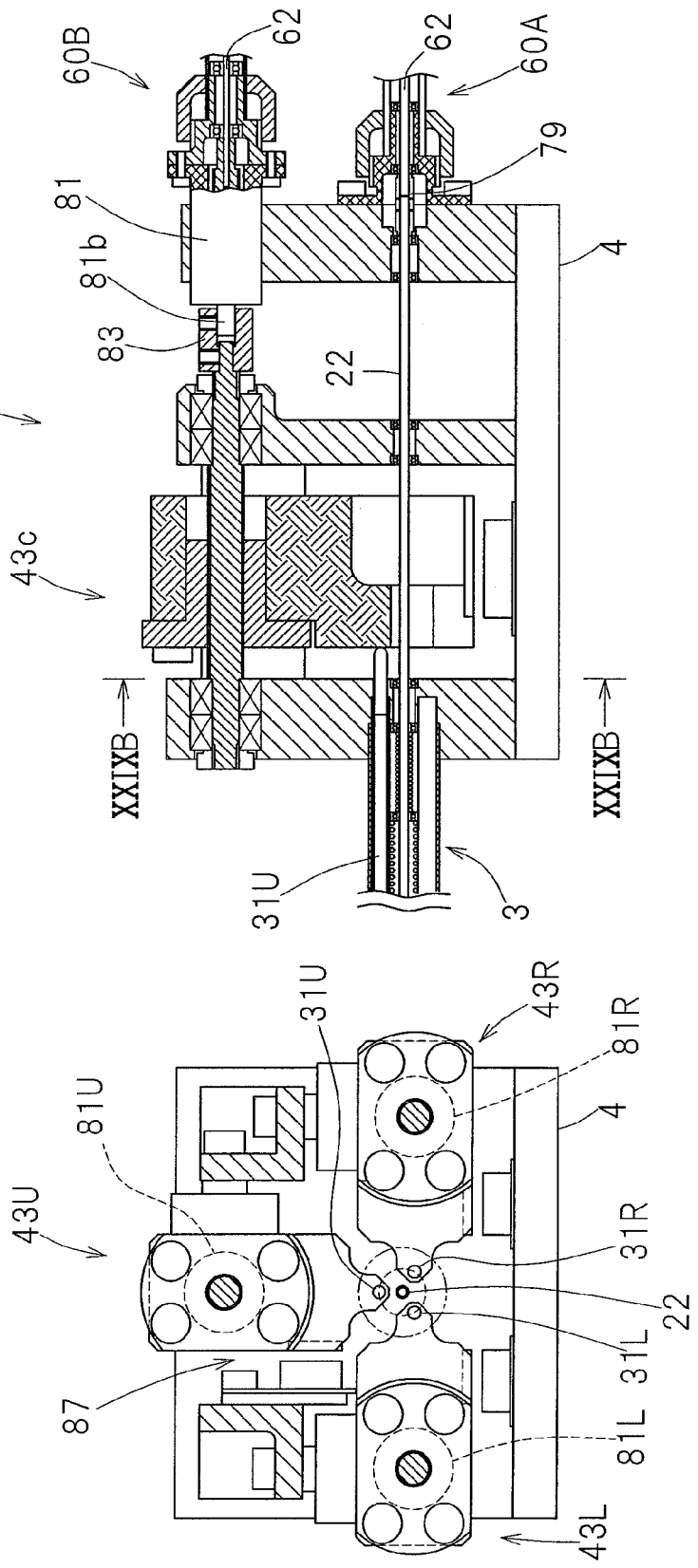

REMOTE CONTROLLED ACTUATOR ASSEMBLY

CROSS REFERENCE TO THE RELATED APPLICATIONS

This application is a U.S. National Phase application of PCT/JP2011/071449 filed Sep. 21, 2011 and claims the foreign priority benefit of Japanese Application No. 2010-220972 filed Sep. 30, 2010 in the Japanese Intellectual Property Office, the contents of both of which are incorporated herein by reference.

BACKGROUND OF THE INVENTION

1. Field of the Invention

The present invention relates to a remote controlled actuator assembly for use in medical and machine processing fields and capable of changing the attitude of a machine tool.

2. Description of Related Art

Remote controlled actuator assemblies are currently available; some are used in the medical field for osteal treatment and some are used in the mechanical processing field for drilling and cutting. Any of those remote controlled actuator assemblies controls by remote control a machine tool fitted to a distal end of an elongated pipe of a linear or curved configuration. However, since the conventional remote controlled actuator assembly is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator assembly will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip joint replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone. It is to be noted that as the actuator assembly for use in the medical field, which does not make use of the elongated pipe, an actuator assembly has also been known (such as disclosed in, for example, the Patent Document 2 listed below), in which a portion of the actuator where a tool is provided relative to another portion of the actuator that is gripped by hand can be altered in attitude.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet this desire, the following technique has hitherto been suggested. For example, the Patent Document 3 listed below discloses the elongated pipe having its intermediate portion curved twice to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 4 listed below discloses the elongated pipe rotated by 180°.

If in a condition, in which the artificial joint is inserted into an artificial joint insertion hole formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever shape the pipe takes, the working range of the tool is limited by the shape of the pipe and, therefore, it is difficult to process the artificial joint insertion hole so that the living bone and the artificial joint may have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator assembly of a type, in which the attitude of the tool coupled to the distal end can be changed by remote control so that the processing of the artificial joint insertion hole can be relatively easily and accurately performed (see, for example, the Patent Documents 5 to 7 listed below). This is because if the attitude of the tool can be changed, the tool can be maintained at a proper attitude regardless of the shape of the pipe.

PRIOR ART LITERATURE

[Patent Document 1] JP Laid-open Patent Publication No. 2007-301149
[Patent Document 2] JP Laid-open Patent Publication No. 2001-17446
[Patent Document 3] U.S. Pat. No. 4,466,429
[Patent Document 4] U.S. Pat. No. 4,265,231
[Patent Document 5] JP Laid-open Patent Publication No. 2010-063876
[Patent Document 6] JP Laid-open Patent Publication No. 2010-069289

[Patent Document 7] JP Laid-open Patent Publication No. 2010-069290

[Patent Document 8] U.S. Pat. No. 5,769,092

However, when a worker such as, for example, a mechanic or a surgeon operates the remote controlled actuator assembly then held in his or her hand, trembling of his or her hands, for example, adversely affect the accuracy with which a tool is positioned relative to an object to be cut. Where the processing is desired to be accomplished with high accuracy, the mechanic or surgeon has to go through many years of experience to acquire the skill. In particular, where a guide portion is of a curved shape, it is difficult to predict the position of the tool provided at a front end of the guide portion and the operation is further complicated and difficult to achieve. In correspondence therewith, the length of cutting time is increased. Where the remote controlled actuator assembly is used for surgical operation during the artificial bone replacement surgery, the increased length of time poses a problem associated with the considerable burden the patient may suffer from.

Because of the reason discussed above, depending on the particular use, there is the need that an actuator main body, which is the remote controlled actuator assembly within the meaning of the above described theme, has to be mounted on an operating bench having one degree of freedom or two or more degrees of freedom so that the adverse influence brought about by the trembling of the hands can be eliminated. This type of the remote controlled actuator assembly is known from, for example, the Patent Document 8 listed above. However, since the conventional remote controlled actuator assembly is of a structure in which the operating bench and the actuator main body are electrically coupled with each other, there is a risk that the actuator main body may be overdriven by an electrical problem to such an extent as to result in injury to the surroundings. Accordingly, in the case of the remote controlled actuator assembly for medical use in which the security is particularly weighted, cases may occur in which the actuator main body is of a structure that can be manipulated by hand.

SUMMARY OF THE INVENTION

In view of the foregoing, the present invention has been devised to provide a remote controlled actuator assembly of a structure which is capable of altering the attitude of a machine tool fitted to a tip end of the actuator main body by remote control and of assuredly supporting the actuator main body, and which is light in weight and the position and the attitude of the actuator main body can be accurately altered by hand.

In order to accomplish the foregoing object of the present invention, there is provided a remote controlled actuator assembly which includes an actuator main body having a tool at a tip end and mounted on an operating bench of a type having an arbitrary degree of freedom; in which the actuator main body comprises a main body base end housing fixed to the operating bench, an elongated spindle guide section having a base end connected with the main body base end housing, and a distal end member fitted to a free end of the spindle guide section through a distal end member connecting unit for alteration in attitude. In such case, the distal end member rotatably supports a spindle to hold the tool, and the spindle guide section includes a rotary shaft to transmit a rotation of a tool rotation drive source to the spindle and a guide hole extending to opposite ends of the spindle guide section. An attitude altering member is reciprocally movably inserted within the guide hole to alter the attitude of the distal end member and is selectively advance or retract with a free end thereof held in contact with the distal end member. An attitude altering drive mechanism is provided within the main body base end housing to selectively advance or retract the attitude altering member when driven by an attitude altering drive source.

According to the above described construction, as a result of rotation of the tool fitted to the distal end member, cutting of the bone or the like takes place. In such case, when the attitude altering member is selectively advanced and retracted one at a time by the attitude altering drive source, the tip end of the attitude altering member works on the distal end member to allow the attitude of the distal end member, fitted to the tip end of the spindle guide section, to alter. The attitude altering drive source for driving the attitude altering drive mechanism is provided at a position distant from the distal end member and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately.

Since the actuator main body is mounted on the operating bench having an arbitrary degree of freedom, the actuator main body can be stably supported at an arbitrary position and in an arbitrary attitude and, therefore, an accurate operation such as, for example, positioning of the tool can be realized. Also, since in dependence on the degree of freedom of the operating bench, the range of operation of the actuator main body is limited and, even in a complicated path, the position and the position and the attitude of the actuator main body can be altered, the positioning accuracy of the tool and the operability thereof increase. In addition, since the position and the attitude of the actuator main body are altered by manual operation, there is no risk that the actuator main body may overdriven against the will of the operator, and, therefore, the safety factor is high.

In the practice of the present invention, it is preferred that the operating bench includes one or both of a revolve pair and a direct acting unit and a freezing mechanism is provided to freeze at least one of the revolve pair or the direct acting unit at an arbitrary position. Even though the operator erroneously leave his or her hand from an operating console of the operating bench, the actuator main body is maintained at a certain attitude by the freezing mechanism and is therefore safe. Also, the labor required for the operator to maintain the actuator main body at the certain attitude can be dispensed and, therefore, the operability increases.

Preferably, the spindle guide section may have a curved portion. That is the reason that if the spindle guide section is curved, the tool can readily make access to a suffering site or the like easily.

Where the spindle guide section has the curved portion as discussed above, the operating bench may include one or more revolve pairs and one of those revolve pairs has the center of rotation coinciding with the center of curvature of the curved portion of the spindle guide section. If the center of rotation of the revolve pair coincides with the center of curvature of the curved portion of the spindle guide section, the spindle guide section moves on a certain circumference relative to the center of rotation of the revolve pair. For this reason, the operator can readily predicate the trajectory of a front end position of the tool and, hence, the operability is good.

In a preferred embodiment of the present invention, the operating bench may include an input side link actuating device to connect an input member relative to a fixing member through three or more sets of input side link mechanisms for alteration in posture, and an output side link actuating device to connect an output member relative to a fixing member through output side link mechanisms, which are equal in number to the number of the sets of the input side link mechanism, for alteration in posture. Each of the input side link mechanisms includes end portion link members on a fixing side and an input side each member having an one end thereof rotatably connected respectively with the fixing member and the input member, an intermediate link member to which the other ends of the respective end portion link members on the fixing side and the input side are rotatably connected, and a geometrical model, in which each of the link members is expressed by a line, representing a shape that a fixing side portion and an input side portion of the intermediate link member relative to a center portion of the intermediate link member are symmetrical with each other. Each of the output side link mechanisms includes end portion link members on a fixing side and an output side each member having an one end thereof rotatably connected respectively with the fixing member and the output member, and an intermediate link member to which the other ends of the respective end portion link members on the fixing side and the output side are rotatably connected.

Each of the output side link mechanisms further includes a geometrical model, in which each of the link members is expressed by a line, representing a shape that a fixing side portion and an output side portion of the intermediate link member relative to a center portion of the intermediate link member are symmetrical with each other. Two or more rotation transmitting mechanisms to transmit a rotation of the end link member on the fixing side in the input side link mechanism to the end link member on the fixing side in the output side link mechanism are provided between the two or more sets of the input side link mechanisms and the output link mechanisms out of the three or more sets of the input side link mechanisms and the output side link mechanisms. The actuator main body is mounted on the output member of the output side link actuating device.

According to the construction described above, the operating bench is of a type provided with the two link actuating devices on the input side and the output side with each link actuating device including the three or more sets of the link mechanisms, and each of the link actuating devices forms a two freedom degree mechanism having the fixing member and the input member or the fixing member and the output member that are movable in two axis directions perpendicular to each other. This two freedom degree mechanism has a large range of movement and capable of accomplishing a smooth movement. By way of example, in the case of the input side link actuating device, the maximum bending angle between the center axis of the fixing member and the center axis of the input member is about ±90° and the angle of swivel of the input member relative to the fixing member can be set to a range of 0 to 360°. This equally applies to the output side link actuating device.

If the input member of the input side link actuating device is moved, the rotation of the end link member on the fixing side of the input side link mechanism is transmitted to the end link member on the fixing side of the output side link mechanism through the two or more rotation transmitting mechanisms, to thereby cause the output member of the output side link actuating device to operate. Since the input side link actuating device and the output side link actuating mechanism are of the same structure, the input member and the output member undergo the same movement. For this reason, where the actuator main body provided in the output member is operated by operating the operating member provided in the input member, the movement of the operating member and the movement of the actuator main body coincide with each other, making it possible to easily operate sensationally. The reason for the use of the two or more rotation transmitting mechanisms is because it is required to fix the operation of the output side link actuating device relative to the operation of the input side link actuating device.

The input side link actuating device and the output side link actuating device are preferably so arranged that the input side link mechanism and the output side link mechanism assume a mirror symmetry relative to each other with respect to the fixing member. If the input side link mechanism and the output side link mechanism assume the mirror symmetry relative to each other, the movement of the input side link actuating device and the movement of the output side link actuating device are also in a mirror symmetry and, therefore, they can be moved in the direction the operator wishes to move and, hence, the operability is good.

Alternatively, the input side link actuating device and the output side link actuating device may be so arranged that the input side link mechanism and the output side link mechanism assume a rotational symmetry relative to each other with respect to the fixing member. If the input side link mechanism and the output side link mechanism assume a rotational symmetry relative to each other, the movement of the input side link actuating device and the movement of the output side link actuating device are also in the rotational symmetry and, therefore, they can be moved in a direction opposite to the direction the operator wishes to move. For this reason, the operator recognizes the fixing member as a movable support and can operate the input side link actuating device so as to move the output side link actuating device, and, hence, the operability is good.

In another preferred embodiment of the present invention, the two or more sets of the input side link mechanism or the output side link mechanism may be provided with a rotational angle detector to detect the angle of rotation of the end link member on the fixing side. Where the rotational angle detector is employed, the attitude of the input side link actuating device or the output side link actuating device can be calculated from an output signal of the rotational angle detector.

Where the rotational angle detector is employed, it is preferred that an angle calculator to calculate the angle of the output member by means of a forward transform of an output signal of the rotational angle detector and an angle display unit to display the angle of the output member calculated by the angle calculator are employed. The use of the angle calculator and the angle display unit makes it possible for the operator to manipulate the input side link actuating device while looking at the current attitude of the output side link actuating device or the output side link actuating device displayed on the angle display unit and, hence, the operability increases.

In a further preferred embodiment of the present invention, one or both of the tool rotation drive source and the attitude altering drive source may be provided in the fixing member and one or both of a flexible tool rotating wire to transmit a rotation of the tool rotation drive source to the rotary shaft and a flexible attitude altering wire to transmit a rotation of the attitude altering drive source to the attitude altering drive mechanism may be provided having been inserted inside the output side link mechanism of the output side link actuating device. The provision of the tool rotation drive source and the attitude altering drive source on the fixing member makes it possible to eliminate the need to use a tool rotation drive source on the actuator main body installed on the output member of the output side link actuating device, and therefore, movable portions including the actuator main body can be reduced in weight and the operability increases accordingly. Also, if the flexible tool rotating wire and the flexible attitude altering wire are provided having been passed through the inside of the output side link mechanism, the flexible wires will not constitute any cause of disturbance and interference and, therefore, the operability is further increased.

In a yet preferred embodiment of the present invention, the attitude altering drive source may be provided in the fixing member, a rotation of this attitude altering drive source is transmitted to an input shaft of the attitude altering drive mechanism through a flexible attitude altering wire. The attitude altering drive mechanism includes a motion converter mechanism to convert a rotation of the input shaft into an advancing and retracting motion, and a center axis of a rotatable portion of the motion converter mechanism is arranged parallel to the input shaft and the rotary shaft at the base end of the spindle guide. According to this construction, since a rotation axis of main body base end housing side end of the flexible attitude altering wire and a rotation axis at the base end of the spindle guide extend parallel to each other, connection of the flexible attitude altering wire and the main body base end housing can be easily accomplished.

In a yet further preferred embodiment of the present invention, each of the flexible tool rotating wire and the flexible attitude altering wire may be of a structure in which within the interior of an outer tube having a flexibility, a flexible inner wire having opposite ends serving respectively as input and output ends of rotation is rotatably supported by a plurality of rolling bearings, and spring elements to apply preloads to the rolling bearings are interposed between the neighboring rolling bearings. The provision of the inner wires, which form respective rotary shafts of the flexible tool rotating wire and the flexible attitude altering wire, within the outer tube makes it possible to protect the inner wires. If each of the inner wires is rotatably supported by the plurality of the rolling bearings and the spring elements are employed between the neighboring rolling bearings, it is possible to suppress the lowering of the natural frequency of the respective inner wires and, therefore, the inner wire can be rotated at a high speed.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 1A is a schematic front elevational view showing a remote controlled actuator assembly according to a first preferred embodiment of the present invention;

FIG. 1B is a schematic side view of a portion of the remote controlled actuator assembly of FIG. 1A;

FIG. 2 is a fragmentary side view showing that portion of the remote controlled actuator assembly on an enlarged scale;

FIG. 3A is a longitudinal sectional view of a distal end member and a spindle guide section of the remote controlled actuator of FIGS. 1A and 1B;

FIG. 3B is a cross sectional view taken along the line IIIB-IIIB in FIG. 3A;

FIG. 3C is a diagram showing a coupling structure between the distal end member and a rotary shaft;

FIG. 22B is a fragmentary longitudinal sectional view showing, on an enlarged scale, a portion of the flexible wire of FIG. 22A, which is encompassed by the circle XXIIB shown in FIG. 22A;

FIG. 22C is a fragmentary longitudinal sectional view showing, on an enlarged scale, another portion of the flexible wire of FIG. 22A, which is encompassed by the circle XXIIC in FIG. 22A;

FIG. 23A is a longitudinal sectional view showing a main body base end housing of the remote controlled actuator assembly;

FIG. 23B is a cross sectional view taken along the line XXIIIB-XXIIIB in FIG. 23A;

FIG. 26A is a longitudinal sectional view showing the distal end member and the spindle guide section of the remote controlled actuator assembly designed in accordance with an eighth preferred embodiment of the present invention, which assembly employs a further different mechanism for altering the attitude of the distal end member;

FIG. 26B is a cross sectional view taken along the line XXVIB-XXVIB in FIG. 26A;

FIG. 29A is a longitudinal sectional view showing another example of the main body base end housing of the remote controlled actuator assembly shown in FIGS. 26A and 26B or FIGS. 27A and 27B; and FIG. 29B is a cross sectional view taken along the line XXIXB-XXIXB in FIG. 29A.

DESCRIPTION OF PREFERRED EMBODIMENTS

Figure 4A:
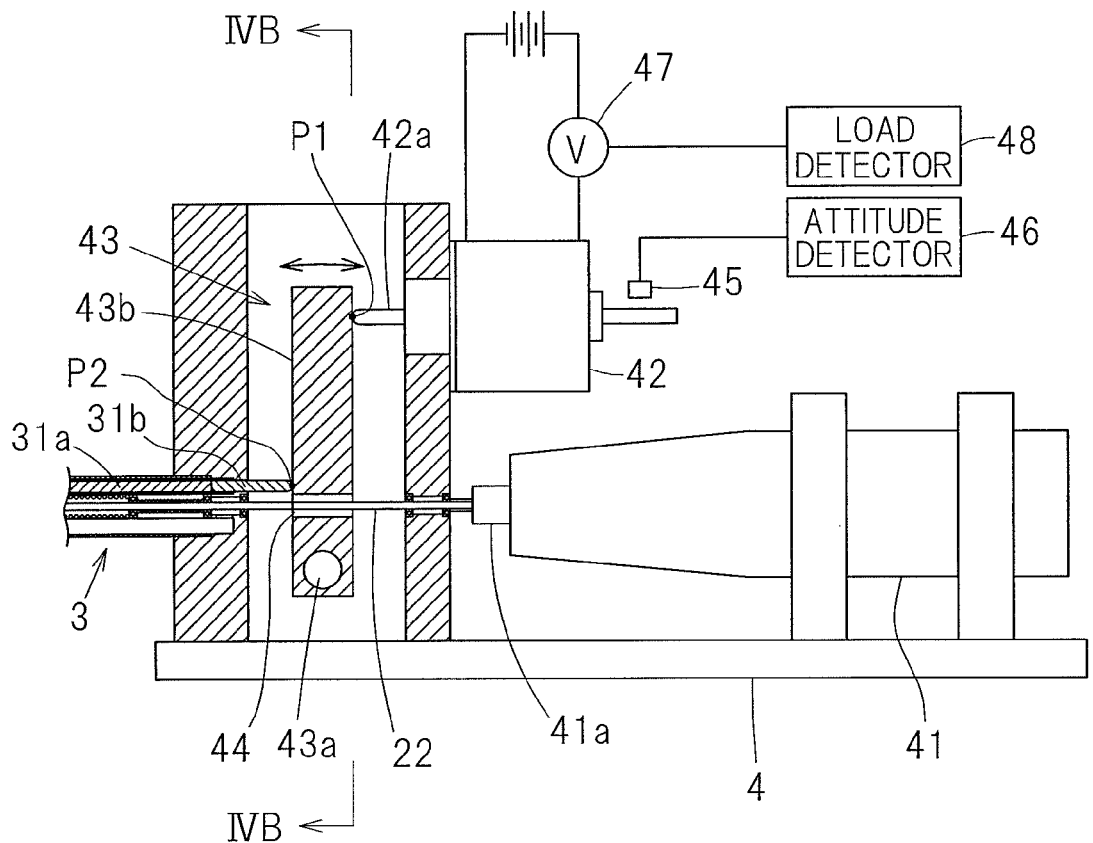
FIG. 4A is a longitudinal sectional view showing a main body base end housing of the remote controlled actuator assembly.

A first preferred embodiment of the present invention will be described in detail with particular reference to FIGS. 1A and 1B to FIGS. 4A and 4B. In particular, FIG. 1A illustrates a front elevational view showing a schematic structure of this embodiment of the present invention, and a remote controlled actuator assembly shown therein is of a type in which an actuator main body 6 having a tip end provided with a rotary tool 1 is mounted on an operating bench 50. The operating bench 50 employed in the practice of this embodiment includes a single direct acting unit 51 and two, first and second revolve pairs 52 and 53. More specifically, the direct acting unit 51 is installed on a horizontal support surface 54, a first member 55 is fixedly provided on a movable stage 51a of the direct acting unit 51, a front end of the first member 55 is connected with a base end of a second member 56 through the first revolve pair 52, and the second member 56 and a mounting carriage 57 are connected with each other through the second revolve pair 53. An operating direction axis of the direct acting unit 51 and a rotary center axis of each of the revolve pairs 52 and 53 are parallel to each other. The direct acting unit 51 is employed in the form of, for example, a ball screw mechanism (not shown) or a linear guide. Also, for each of the revolve pairs 52 and 53, a rolling bearing assembly or a slide bearing assembly, for example, is employed.

The mounting carriage 57 is of an L-shaped confirmation, when viewed from front, except for a portion thereof including the second revolve pair 53, and is made up of first and second flat portions 57a and 57b connected together or formed integrally with each other so as to represent the L-shaped configuration. The first flat portion 57a of the mounting carriage 57 has a main body base end housing 4 of the actuator main body 6 fixedly mounted thereon and an operating member 58 is fitted to the second flat portion 57b of the mounting carriage 57. When the operating member 58 is manipulated, the direct acting unit 51 and the revolve pairs 52 and 53 are operated to change the position and the attitude of the actuator main body 6. It is, however, to be noted that the direct acting unit 51 and the first and second revolve pairs 52 and 53 may be operated by means of a drive source (not shown) such as, for example, a motor on the basis of a command given by an operator.

As shown in FIG. 2, the first revolve pair 52 is provided with a freezing mechanism 59 for freezing the first revolve pair 52 at an arbitrary position. The first revolve pair 52 employed in the instance as shown has a revolve pair shaft 52a fixedly mounted on the first member 55 and supports the second member 56 by means of a bearing (not shown) so that the second member 56 can rotate about the revolve pair shaft 52a. The freezing mechanism 59 includes a freezing member 59a having an externally threaded shank 59aa that is engageable in an internally threaded hole 55a defined in the first member 55 so as to extend completely therethrough, and is of a structure in which when a front end of the freezing member 59a is brought into contact with a side face of the second member 56, the second member 56 can be restricted from rotating relative to the first member 55.

The use of the freezing mechanism 59 of the kind discussed above is useful in that even when the operator erroneously leaves his or her hand from the operating member 58 of the operating bench 50, the attitude of the actuator main body 6 mounted on the mounting carriage 57 can be maintained constant for safety purpose. Also, there is no need for the operator to make efforts to maintain the actuator main body 6 at a constant attitude, resulting in an increase of the operability. It is, however, to be noted that the site at which the freezing mechanism 59 is disposed may not necessarily be limited to the first revolve pair 52, but may be the direct acting unit 51 or the second revolve pair 53.

As best shown in FIG. 1A, the actuator main body 6 includes a front end or distal end member 2 for holding the rotary tool 1, an elongated spindle guide section 3 having a front end to which the distal end member 2 is fitted for alteration in attitude thereof, a main body base end housing 4 with which a base end of the spindle guide section 3 is connected, and a controller 5 for controlling a tool rotation drive source 41 and an attitude altering drive source 42 both within the main body base end housing 4. The controller 5 referred to above may, however, be disposed separate from the main body base end housing 4.

An internal structure of each of the distal end member 2 and the spindle guide section 3 will be described in detail with particular references to FIGS. 3A to 3C. The distal end member 2 includes a generally or substantially cylindrical housing 1 and a spindle 13 rotatably accommodated within such cylindrical housing 1 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member connecting unit 15. The distal end member connecting unit 15 supports the distal end member 2 for displacement in attitude and is comprised of a spherical bearing. More specifically, the distal end member connecting unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. In the instance as shown, since the construction is so employed that the distal end member 2 can alter its attitude about an X-axis passing through the center O of curvature, the guide faces F1 and F2 may be cylindrical surface each having its longitudinal axis represented by the X-axis passing through the center O of curvature.

The spindle guide section 3 includes a rotary shaft 22 for transmitting a rotational force exerted by a tool rotating drive source 41 (FIG. 1A) accommodated within the main body base end housing 4. This rotary shaft 22 is provided in a region ranging from the spindle guide section 3 to the main body base end housing 4 (best shown in FIG. 1A), with its base end positioned in the vicinity of the base end of the main body base end housing 4. In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 3C, the spindle 13 and the rotary shaft 22 are coupled together by means of a universal joint 23 for transmitting rotation from the rotary shaft 22 to the spindle 13. The universal joint 23 is made up of a groove 13a, defined in a closed base end of the spindle 13, and of a projection 22a defined in a distal end of the rotary shaft 22 and engageable in the groove 13a. The center of joint between the groove 13a and the projection 22a is located at the same position as the centers of curvature O of the guide faces F1 and F2.

The spindle guide section 3 has an outer shell pipe 25, which forms an outer shell of the spindle guide section 3, and the rotary shaft 22 referred to above is positioned at a center of this outer shell pipe 25. The rotary shaft 22 so positioned is rotatably supported by a plurality of rolling bearings 26 positioned spaced a distant apart from each other in a direction axially of the spindle guide section 3. Between the neighboring rolling bearings 26, spring elements 27A for generating a preload on the inner rings of the corresponding rolling bearing 26 and spring elements 27B for generating the preload on the outer rings of the corresponding rolling bearings 26 are alternately disposed relative to each other. Those spring elements 27A and 27B may be employed in the form of, for example, compression springs. The constraint member 21 referred to previously is fixed to a pipe end portion 25a of the outer shell pipe 25 by means of a fixing pin 28 and has its distal end inner peripheral portion supporting a distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

Provided between an inner diametric surface of the outer shell pipe 25 and the rotary shaft 22 is a guide pipe 30, having its opposite ends opening. Within a guide hole 30a which is an inner diametric hole of this guide pipe 30, an attitude altering member 31 is reciprocally movably inserted. In the instance as shown, the attitude altering member 31 is in the form of a wire 31a and pillar shaped pins 31b connected to a tip end of the wire 31a. The attitude altering member 31 has a tip end representing a spherical shape which is held in contact with a base end face of the housing 11 of the distal end member 2. The other of the pillar shaped pins 31b that is closer to the main body base end housing 4 also has a tip end representing a spherical shape which is held in contact with a front surface of a lever 43b (FIG. 4A and FIG. 4B) which will be explained in detail later.

Between a base end face of the housing 11 of the distal end member 2 and a tip end face of the outer shell pipe 25 of the spindle guide section 3, a restoring elastic member 32 made of, for example, a compression coil spring, is arranged at a location spaced 180° degrees circumferentially in phase from the circumferential location where the attitude altering member 31 is positioned. The restoring elastic member 32 biases the distal end member 2 towards a predetermined attitude.

Also, as shown in FIG. 3B, a plurality of reinforcement shafts 34 are arranged, separate from the guide pipe 30, between the inner diametric surface of the outer shell pipe 25 and the rotary shaft 22 and on the same pitch circle C as that depicted by the guide pipe 30. Those reinforcement shafts 34 are employed for securing the rigidity of the spindle guide section 3. The guide pipe 30 and the plural reinforcement shafts 34 are spaced an equal distance from each other. The guide pipe 30 and the plural reinforcement shafts 34 are held in contact with the inner diametric surface of the outer shell pipe 25 and an outer diametric surface of each of the rolling bearings 26 so as to support the respective outer diametric surfaces of the rolling bearings 26.

Figure 4B:
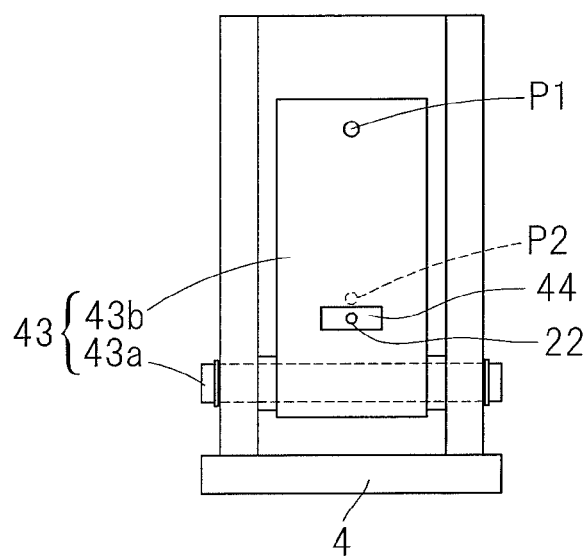
FIG. 4B is a cross sectional view taken along the line IVB-IVB in FIG. 4A.

FIGS. 4A and 4B illustrate an internal structure of the main body base end housing 4. Referring now to those figures, the main body base end housing 4 accommodates therein the tool rotation drive source 41 and the attitude altering drive source 42. The tool rotation drive source 41 is in the form of, for example, an electrically driven motor having its output shaft 41a coupled with a base end of the rotary shaft 22. The rotary shaft 22 is made to extend through an opening 44 defined in the pivot lever 43b to be hereinafter described. The attitude altering dive source 42 is in the form of, for example, an electrically driven actuator, and the movement of an output rod 42a, which is a linear motion member capable of selectively advancing and retracting, i.e., reciprocally movable in a direction leftwards and rightwards as viewed in FIG. 4A, is transmitted to the attitude altering member 31 through an attitude altering drive mechanism 43. The attitude altering drive mechanism 43 includes a pivot lever 43b pivotable about a support pin 43a and is so designed and so configured as to allow a force of the output rods 42a to work on a working point P1 of the levers 43b, which are respectively spaced a long distance from the support pin 43a, and as to apply a force to the attitude altering members 31 at a force point P2, which are spaced a short distance from the support pin 43a, wherefore the outputs of the attitude altering drive sources 42 can be increased and then transmitted to the attitude altering members 31. In other words, the attitude altering drive mechanism 43 employed in the practice of this embodiment is a force increasing and transmitting mechanism. It is also to be noted that in place of the use of, for example, the electrically driven actuator, the attitude of the distal end member 2 may be manually altered by remote control.

The main body base end housing 4 is provided with an actuation amount detector 45 for detecting the amount of actuation of the attitude altering drive source 42. A detected value of this actuation amount detector 45 is fed to an attitude detector 46. The attitude detector 46 then detects an inclined attitude of the distal end member 2 about the X axis (FIG. 3B) in reference to an output of the actuation amount detector 45. The attitude detector 46 includes a relation setting unit (not shown), in which relations between the inclined attitude and the input signal of the actuation amount detector 45 are set in terms of calculating equations and/or tables so that the inclined attitude can be detected in reference to the inputted output signal with the use of the relation setting unit. It is to be noted that this attitude detector 46 may be provided either inside the controller 5 or in an external control device.

The main body base end housing 4 is provided with a supply power meter 47 for detecting the electric energy supplied to the attitude altering drive source 42, which is an electrically operated actuator, independent of each other. The detection value of this supply power meter 47 is outputted to a load detector 48. This load detector 48 in turn detects a load acting on the distal end member 2 in reference to the outputs of the supply power meter 47. Specifically, this load detector 48 includes a relation setting unit (not shown), in which the relation between the load and the output signal of the supply power meter 47 is set in terms of an arithmetic equation or table, and makes use of the relation setting unit to detect the load in reference to the output signal so inputted. This load detector 48 may be provided either in the controller 5 (FIGS. 1A and 1B) or in an external control device.

The controller 5 (shown in FIGS. 1A and 1B) includes a control device comprised of a computer and a program executed thereby and is operable on the basis of the respective detection values of the attitude detector 46 and the load detector 48 to control the tool rotation drive source 41 and the attitude altering drive source 42. Control contents will be described in detail later.

The operation of this remote controlled actuator assembly of the structure hereinabove described will be described with particular reference to FIGS. 1A and 1B. The actuator main body 6 is mounted on the operating bench 50 and is therefore supported stably at an arbitrary position and in an arbitrary posture. Since the operating bench 50 has the direct acting unit 51 and the two revolve pairs 52 and 53, by operating the operating member 58 of the operating bench 50, the position and the attitude of the actuator main body 6 can be altered. Since the range of operation of the actuator main body 6 is limited and the position and the attitude of the actuator main body 6 can be accurately operated even in a complicated route, the positioning accuracy and operability of the tool 1 are good. Also, since the position and the attitude of the actuator main body 6 are altered by a manual operation, there is no risk that the actuator main body 6 may be overdriven against the will of the operator and, therefore, the safety factor is high.

When the tool rotation drive source 41 is driven, the rotational force thereof is transmitted to the spindle 13 through the rotary shaft 22 to thereby rotate the tool 1 together with the spindle 13. The load acting on the distal end member 2 when the tool 1 then being rotated cuts a bone or the like is estimated from the detection value of the supply power meter 47, shown in FIG. 4A, by the load detector 48. Accordingly, when the amount of feed of the actuator main body 6 and the alteration of attitude of the distal end member 2 are controlled in dependence on the value of the load detected in the manner described above, cutting of the bone can be properly carried out while the load acting on the distal end member 2 is maintained properly.

During the use, the attitude altering drive source 42 is driven and the attitude alteration of the distal end member 2 is performed by remote control. By way of example, as shown in FIG. 3A, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 3A. If the attitude altering member 31 is conversely retracted, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 3A. At this time, a pressure from the attitude altering member 31, the elastic repulsive force from the restoring elastic member 32 and a reactive force from the constraint member 21 are applied to the distal end member connecting unit 15 and, depending on the balance of those applied forces, the attitude of the distal end member 2 is determined. The attitude of the distal end member 2 is then detected by the attitude detector 46 from the detection value of the actuation amount detector 45 shown in FIG. 4A. For this reason, the attitude of the distal end member 2 can be properly controlled by remote control.

Since the attitude altering member 31 is inserted through the guide hole 30a of the guide pipe 30, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

The remote controlled actuator assembly of the foregoing construction is utilized in grinding the femoral marrow cavity during, for example, the artificial joint replacement surgery and during the surgery, it is used with the distal end member 2 in its entirety or a part thereof inserted into the body of a patient. Because of this, with such distal end member 2 as described above that can be altered in attitude by remote control, the bone can be processed in a condition with the tool 1 maintained in a proper attitude at all times and the opening for insertion of the artificial joint can be finished accurately and precisely. Since the actuator main body 6 is supported in a stabilized fashion, the operation is easy to accomplish and the length of processing time can be reduced. In view of this, where the remote controlled actuator assembly is used for surgical purpose, the burden on the patient can be relieved.

There is the necessity that the rotary shaft 22 and the attitude altering member 31 are provided within the spindle guide section 3 of an elongated shape in a protected fashion. Hence, the rotary shaft 22 is provided in the center portion of the outer shell pipe 25 and the guide pipe 30, in which the attitude altering member 31 is accommodated, and the reinforcement shafts 34 are arranged between the outer shell pipe 25 and the rotary shaft 22 so as to be juxtaposed in the circumferential direction. Accordingly, it is possible to protect the rotary shaft 22 and the attitude altering member 31 and, at the same time, the interior can be made hollow to thereby reduce the weight without sacrificing the rigidity. Also, the balance of the remote-controlled actuator assembly as a whole is good.

Since the outer diametric surfaces of the rolling bearings 26 supporting the rotary shaft 22 are supported by the guide pipes 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

Figure 5:
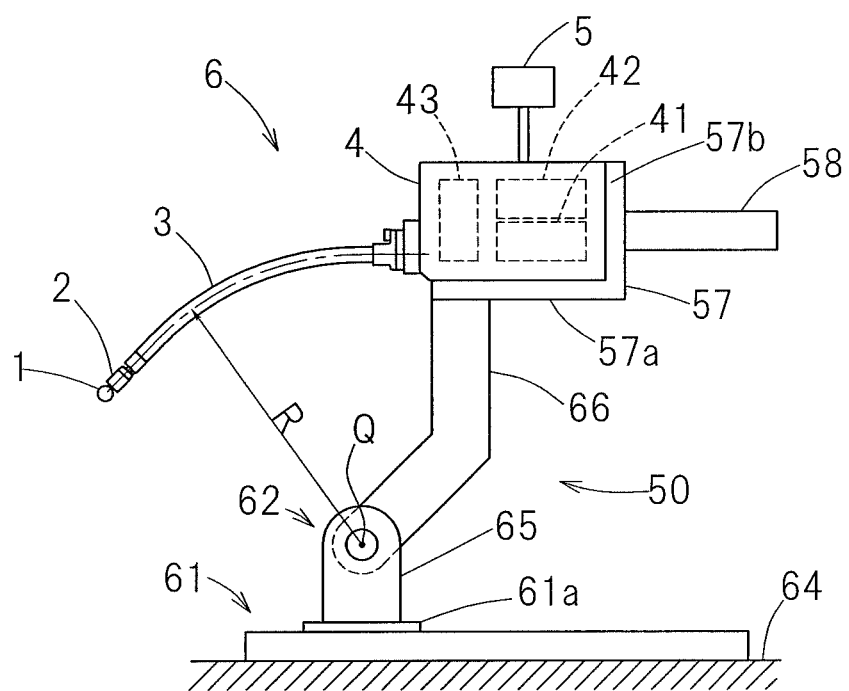
FIG. 5 is a schematic front elevational view showing the remote controlled actuator assembly according to a second preferred embodiment of the present invention.

Although the actuator main body 6 shown in FIG. 1A makes use of the spindle guide section 3 that is of a rectilinear shape, the attitude altering member 31 is flexible, and therefore, the attitude altering operation of the distal end member 2 can be assuredly accomplished even though the spindle guide section 3 is curved as shown in FIG. 5. It is, however, to be noted that only a portion of the spindle guide section 3 may be of a curved shape. If the spindle guide section 3 has a curved shape, it may occur that insertion of the distal end member 2 deep into the bore, where the spindle guide section of the rectilinear shape fails to reach, can be accomplished. Therefore, the processing of the artificial joint insertion hole for the artificial joint replacement surgery can be formed precisely and accurately.

Where the spindle guide section 3 is of the curved shape, the outer shell pipe 25, the guide pipe 30 and the reinforcement shafts 34 have to be curved correspondingly. Also, the rotary shaft 22 is preferred to make use of an easily deformable material and the use of a shape memory alloy is suitable.

The remote controlled actuator assembly designed in accordance with a second preferred embodiment of the present invention is shown in FIG. 5. The remote controlled actuator assembly shown in FIG. 5 differs from the remote controlled actuator assembly of the structure shown in and described with particular reference to FIG. 1A, in respect of not only the details of the actuator main body 6 but also the details of the operating bench 50. Specifically, the operating bench 50 employed in the practice of the second embodiment has a single direct acting unit 61 and a single revolve pair 62. More specifically, the direct acting unit 61 is installed on a horizontal support surface 64, a first member 65 is fixedly mounted on a movable stage 61a of the direct acting unit 61, a front end of the first member 65 and a base end of a second member 66 are connected with each other through the revolve pair 62, and a mounting carriage 57 is fixed to a front end of the second member 66. An operating direction axis of the direct acting unit 61 and a revolve center axis of the revolve pair 62 lie perpendicular to each other.

Also, in this second embodiment, the center of curvature Q of the spindle guide section 3 of the actuator main body 6 and the center of revolution of the revolve pair 62 coincide with each other. Accordingly, the spindle guide section 3 moves along a certain circumference spaced a distance equal to the radius of curvature R from the center of revolution of the revolve pair 62 and, therefore, the operator can easily foresee the trajectory of a front end position of the tool 1 and, hence, the operability is good.

Figure 6:
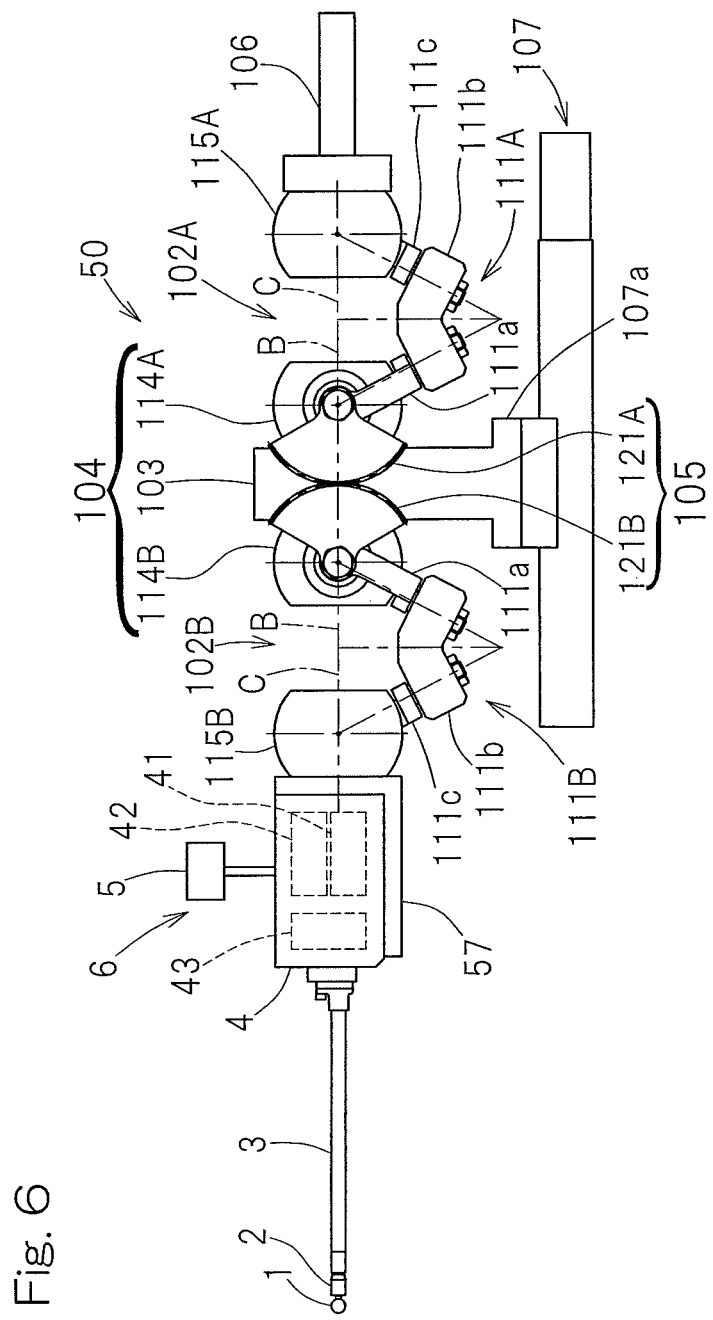
FIG. 6 is a front elevational view, with a portion removed, showing the remote controlled actuator assembly according to a third preferred embodiment of the present invention.

FIGS. 6 to 11 illustrate a third preferred embodiment of the present invention. As shown in FIG. 6, the operating bench 50 used with the remote controlled actuator assembly includes two, input side and output side link actuating devices 102A and 102B. Respective fixing members 114A and 114B of those link actuating devices 102A and 102B are fixed to a common fixing trestle 103. In a broad sense, the two fixing members 114A and 114B and the fixing trestle 103 cooperate with each other to define a "fixing member". In the description that follows, the fixing member in that broad sense is referred to as "broad fixing member 104". It is to be noted that the fixing member referred to in the appended claims stands for this "broad fixing member 104".

Figure 7:
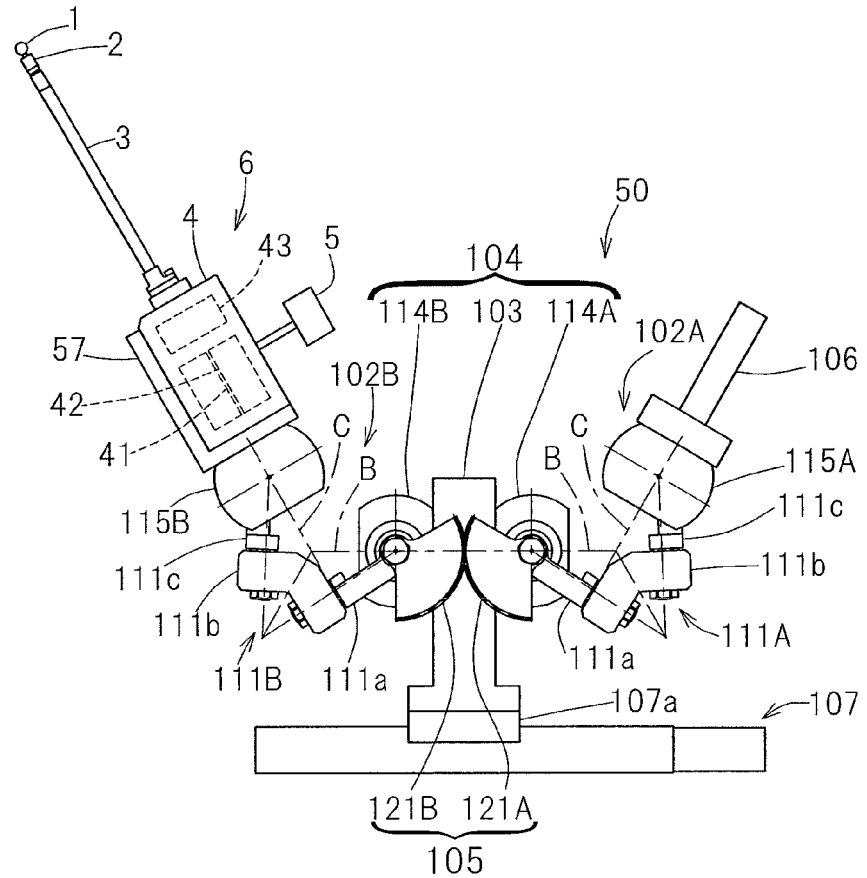
FIG. 7 is a front elevational view, with a portion removed, of the remote controlled actuator assembly of FIG. 6, showing a different condition thereof.
Figure 8B:
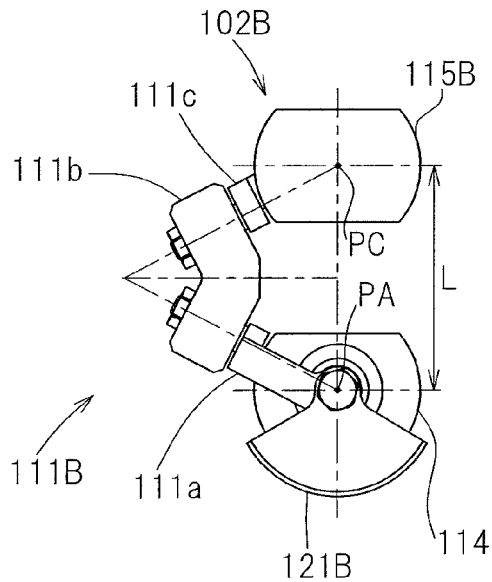
FIG. 8B is a front elevational view, with a portion removed, showing an output side link actuating device employed in the remote controlled actuator assembly of FIG. 6.
Figure 8A:
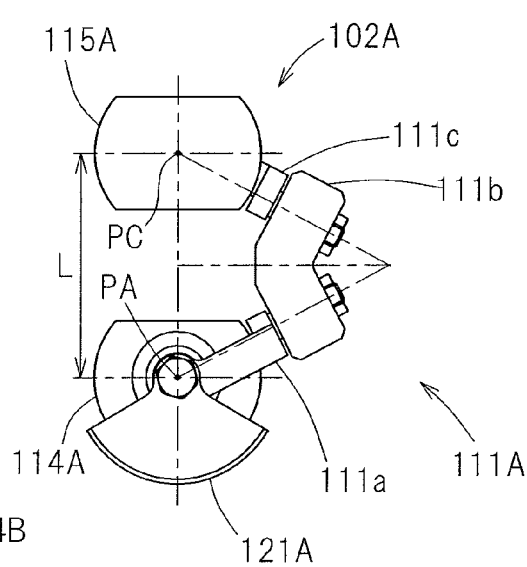
FIG. 8A is a front elevational view, with a portion removed, showing an input side link actuating device employed in the remote controlled actuator assembly of FIG. 6.

As shown in FIG. 8A, the input side link actuating device 102A is the one in which an input member 115A is drivingly connected with the fixing member 114A through three sets of input side link mechanisms 111A to 113A for alteration in attitude. As shown in FIG. 8B, the output side link actuating device 102B is the one in which an output member 115B is drivingly connected with the fixing member 114B through three sets of output side link mechanisms 111B to 113B. The link actuating devices 102A and 102B are so arranged and so positioned that the input side link mechanism 111A and the output side link mechanism 111B can assume a mirror symmetry relative to the broad fixing member 104. Except for this point, the link actuating devices 102A and 102B are basically of the same structure. It is to be noted that in FIG. 6 to FIGS. 8A and 8B, of the three sets of the input side link mechanisms and the three sets of the output side link mechanisms, only one input side link mechanism 111A and only one output side link mechanism 111B are shown.

Figure 9:
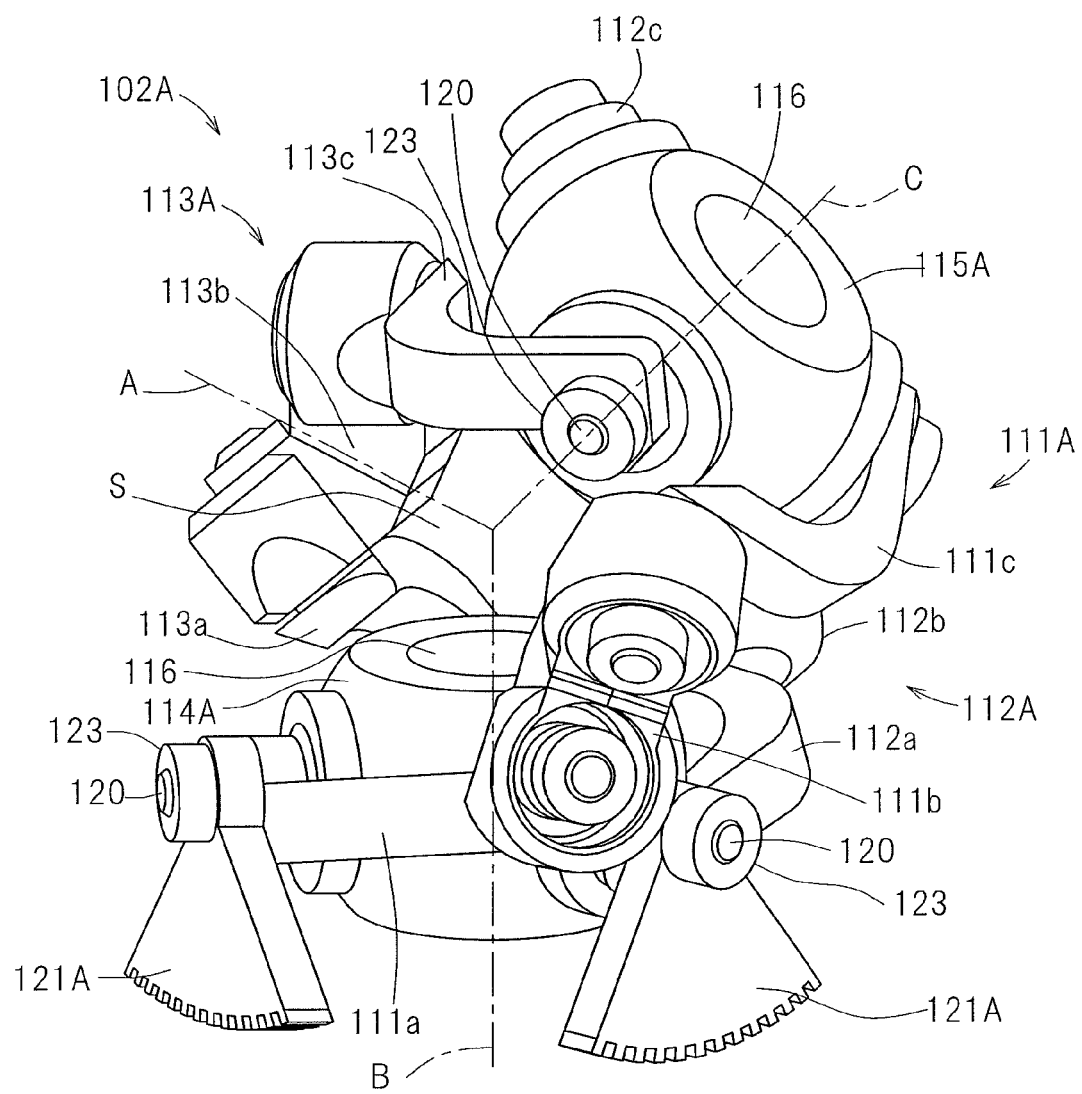
FIG. 9 is a perspective view of the input side link actuating device shown in FIG. 8A.
Figure 10:
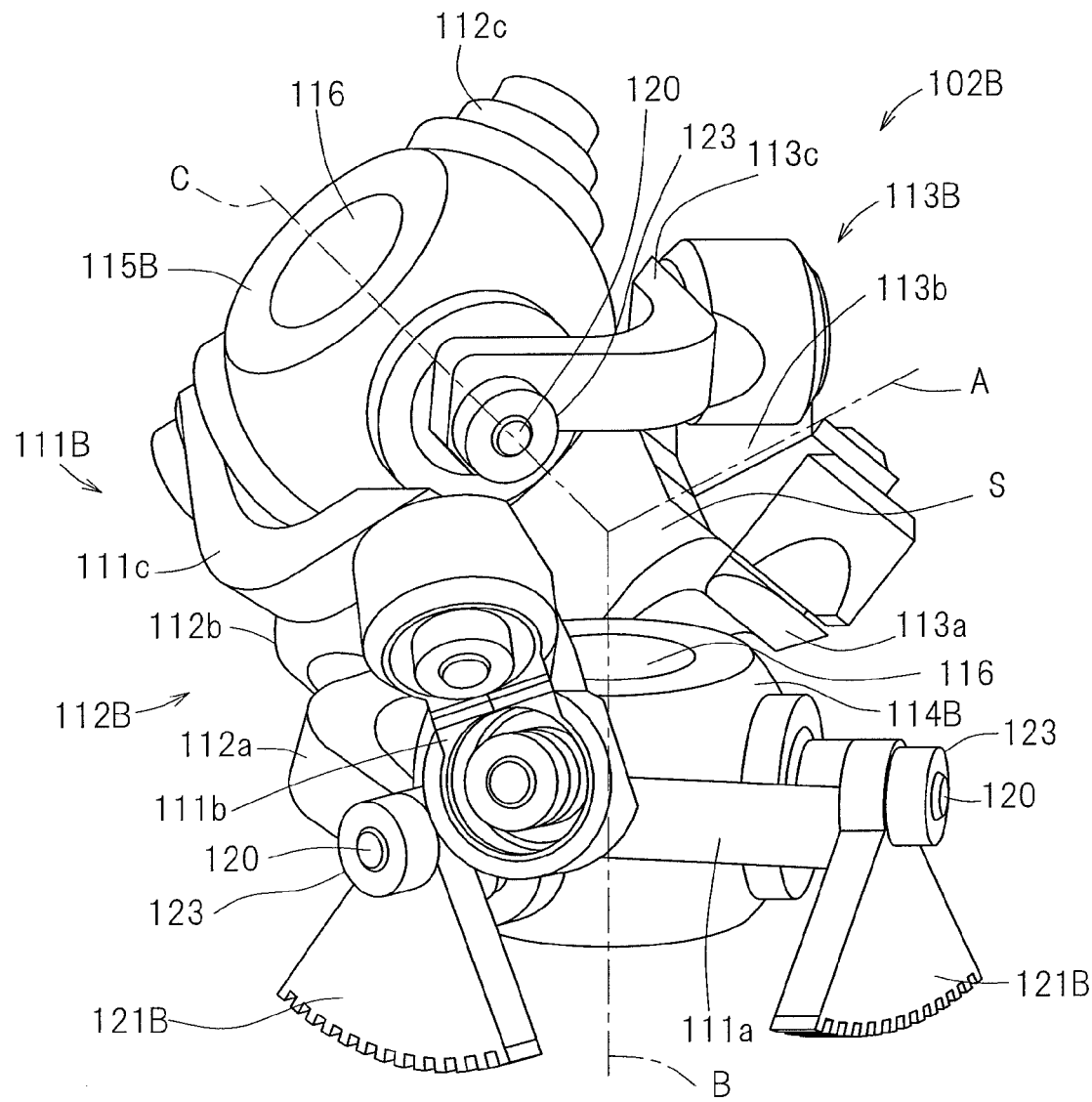
FIG. 10 is a perspective view of the output side link actuating device shown in FIG. 8B.

FIG. 9 illustrates a perspective view of the input side link actuating device 102A and FIG. 10 illustrates a perspective view of the output side link actuating device 102B. As hereinbefore explained, since the link actuating devices 102A and 102B are of the same structure except for the mirror symmetrical disposition of the link mechanisms 111A and 111B, in the following description only the input side link actuating device 102A will be described for the sake of brevity, noting that component parts of the output side link actuating device 102B, which are similar to those of the input side link actuating device 102A, are designated by reference numerals in parentheses following the reference numerals used to denote such similar components of the input side link actuating device 102A.

The input side link actuating device 102A (output side link actuating device 102B) includes three sets of input side link mechanisms 111A, 112A and 113A (output side link mechanisms 111B, 112B and 113B). Hereinafter, the respective input side link mechanisms 111A, 112A and 113A (output side link mechanisms 111B, 112B and 113B) are designated by 111A to 113A (111B to 113B). The three sets of those link mechanisms 111A to 113A (111B to 113B) have respective shapes that are geometrically identical with each other. In other words, each of the link mechanisms 111A to 113A (111B to 113B) is of such a shape that geometric models of each of link members 111a to 113a, 111b to 113b and 111c to 113c, when schematically expressed by lines, is such that an input side portion and an output side portion relative to an intermediate portion of the intermediate link members 111b to 113b are symmetrical to each other.

Each of the link mechanisms 111A, 112A and 113A (111B, 112B and 113B) is made up of an end portion link member 111a, 112a and 113a on the fixing side, an intermediate link member 111b, 112b and 113b and an end portion link member 111c, 112c and 113c on an input side (output side), and forms a three-link chain mechanism comprised of four revolve pairs. Hereinafter the respective link members are designated as 111a to 113a, 111b to 113b and 111c to 113c. Each of the end portion link members 111a to 113a, 111b to 113b on the fixing side and the end portion link members 111c to 113c on the input side (output side) is of a spherical surface link structure. The former three link members 111a to 113a have a common spherical surface link center PA and the latter three link members 111c to 113c have a common spherical surface link center PC. In each of the three link mechanism 111A to 113A (111B to 113B), distances from the associated center PA or PC to the respective three end portion link members 111a to 113a or 111c to 113c are the same. The axes of the revolute pairs, which define joints between the end portion link member 111a to 113a or 111c to 113c and the intermediate link member 111b to 113b may have a certain crossed axes angle or may be parallel to each other. It is, however, to be noted that the respective shapes of the intermediate link members 111b to 113b in the three sets of the link mechanisms 111A to 113A (111B to 113B) are geometrically identical with each other.

One set of the link mechanism 111A to 113A (111B to 113B) includes the fixing member 114A (114B), the input member 115A (output member 115B), the two end portion link members 111a to 113a and 111c to 113c rotatably connected with the fixing member 114A (114B) and the input member 115A (output member 115B), respectively, and the intermediate link member 111b to 113b connected rotatably with the respective end portion link members 111a to 113a and 111c to 113c and connecting the two end portion link members 111a to 113a and 111c to 113c together.

The link mechanism 111A to 113A (111B to 113B) employed in this preferred embodiment is of a rotation symmetrical type and the positional relation between a fixing side group of the fixing member 114A (114B) and the end portion link member 111a to 113a and an output side (output side) group of the input member 115A (output member 115B) and the end portion link member 111c to 113c is such as to form a positional construction in which the positional relation is rotationally symmetrical with respect to a center line A of the intermediate link member 111b to 113b. FIG. 6 illustrates a condition in which a center axis B of the fixing member 114A (114B) and a center axis C of the input member 115A (output member 115B) lie on the same line and FIG. 7 illustrates a condition in which the center axis C of the input member 115A (output member 115B) relative to the center axis B of the fixing member 114A (114B) assumes a predetermined working angle. Even when each of the link mechanisms 111A to 113A (111B to 113B) changes in its posture, the distance L (FIGS. 8A and 8B) between the spherical surface link centers PA and PC on the fixing side and the input side (output side) does not change.

Figure 11:
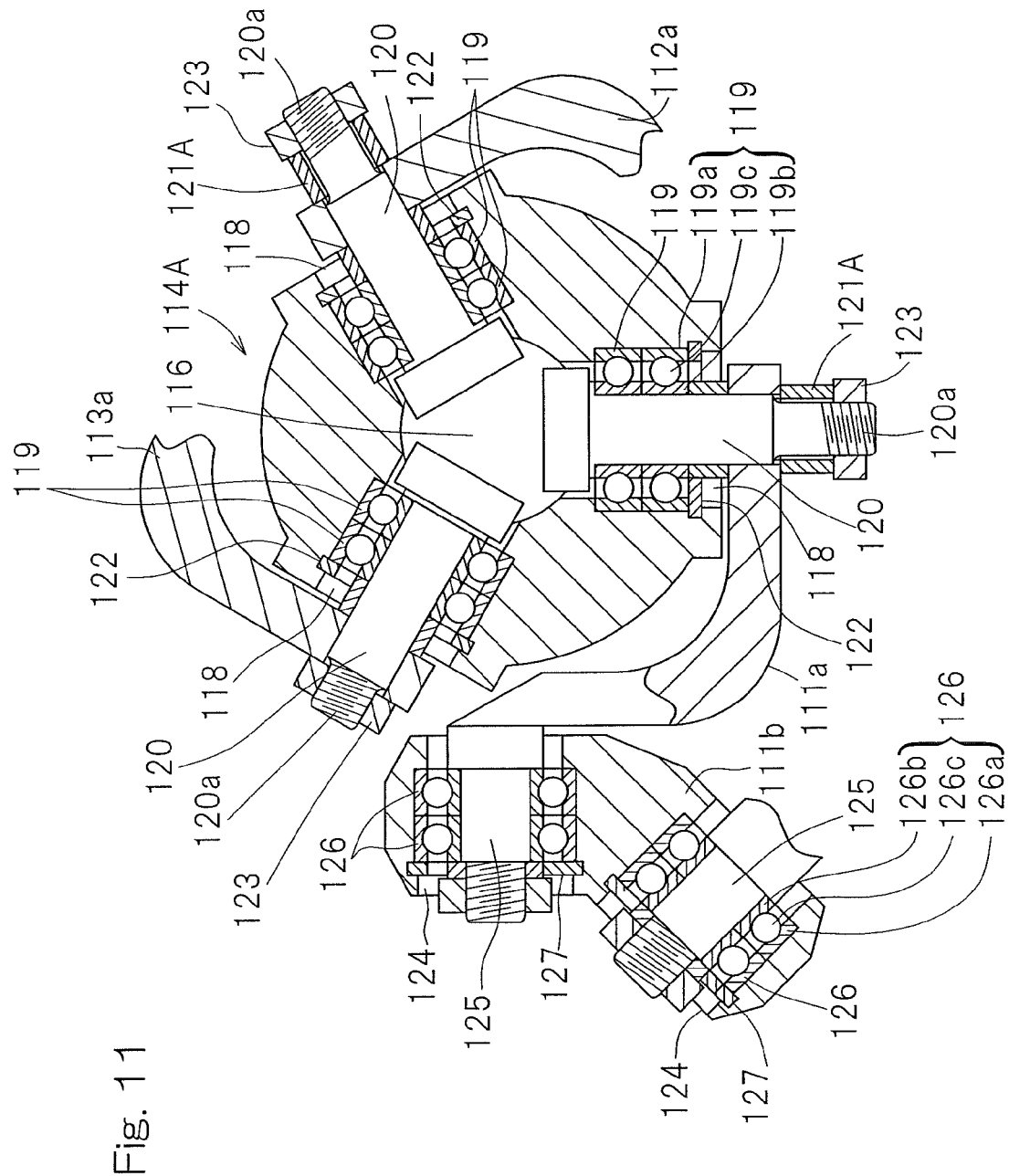
FIG. 11 is a longitudinal sectional view showing a fixing member, an end link member on a fixing side and an intermediate link member of the input side link actuating device.

As shown in FIG. 11, the fixing member 114A (114B) is of a structure having its center portion formed with a throughhole 116 so as to extend in an axial direction and having an outer appearance so shaped as to represent the shape of a ring-shaped doughnut. The fixing member 114A (114B) is provided with circumferentially equally spaced through holes 118 for the insertion of respective shaft members therethrough so as to extend in a radial direction and the shaft members 120 are inserted into the throughholes 118 through associated bearings 119. The input member 115A (output member 115B) is of a structure similar to that of the fixing member 114A (114B) with a throughhole 116 (shown in FIGS. 9 and 10) defined in its center portion so as to extend in an axial direction.

Each of the bearings 119 is employed in the form of, for example, a deep groove ball bearing and is made up of an outer ring 119a inserted into the corresponding throughhole 118 in the fixing member 114A (114B), an inner ring 119b mounted externally on the shaft member 120, and rolling elements 119c such as, for example, balls that are rollingly interposed between the outer ring 119a and the inner ring 119b. In other words, the outer ring 119a is fixed to the fixing member 114A (114B) and the inner ring 119b is rotatable together with the shaft member 120. The shaft member 120 has an one end portion protruding outwardly from the fixing member 114A (114B); and the end portion link member 111a, 112a or 113a is connected with a projecting threaded portion 120a of the respective shaft member 120 and fixed by means of a nut 123, fastened to the shaft member 120, with a predetermined preload amount having been applied to the associated bearing 119. The bearing 119 for supporting the shaft member 120 rotatably relative to the fixing member 114A (114B) is locked in position on the fixing member 114A (114B) by means of a retaining ring 122 so as not to separate from the fixing member 114A (114B). It is to be noted that for the bearing 119, an angular contact ball bearing, a roller bearing or a slide bearing can be employed other than such deep groove ball bearing as shown in FIG. 11.

Also, of the three shaft member 120 provided in the fixing member 114A (114B), the two shaft members 120 connected respectively with the end rink members 111a, 112a are provided with respective gear members 121A (121B) between the end rink members 111a, 112a and the corresponding nuts 123 for rotation together with the associated shaft members 120. The gear members 121A (121B) are employed in the form of sector shaped spur gears as best shown in FIGS. 6 to 10. Those gear members 121A and 121B are of the same diameter and have the same pitch with the mating members meshed with each other.

The shaft member 120 and the end portion link member 111a to 113a are connected by means of, for example, a crimping technique. Alternatively, connection can be accomplished by the use of keys or serrations. In such case, an undesirable loosening of the connecting structure can be prevented and the transmitting torque can be increased. Also, each shaft member 120 and the associated gear member 121A (121B) may be splined to each other so that the both can rotate together.

The input member 115A (output member 115B) is of a structure identical with that of the fixing member 114A (114B), except that no gear member 121 is provided in an outer end portion of the shaft member 120. Respective circumferential positions of the shaft members 120 may not necessarily be spaced equidistantly from each other in the circumferential direction, but it is necessary that the fixing member 114A (114B) and the input member 115A (output member 115B) must have the same positional relation with each other in the circumferential direction. The fixing member 114A (114B) and the input member 115A (output member 115B) are commonly shared by the three sets of the link mechanisms 111A to 113A (111B to 113B), and the end portion link member 111a to 113a and 111c to 113c are connected with each of the shaft members 120.

Each of the end portion link members 111a to 113a and 111c to 113c is of an L-shaped configuration having one side, connected with the associated shaft member 120, which protrudes outwardly from the fixing member 114A (114B) or the input member 115A (output member 115B), and the other side connected with the intermediate link member 111b to 113b. Each of the end portion link members 111a to 113a and 111c to 113c is of a shape, in which a bent base end inside of a shank portion 125, which is positioned on the side of a link center, is largely cut out so that a large moving angle can be obtained.

The intermediate link member 111b to 113b is of a substantially L-shaped configuration having a throughhole 124 defined in its both sides. This intermediate link member 111b to 113b is of such a shape that its peripheral side face is largely cut out to enable it to have a large moving angle. The shank portion 125 integrally formed to bend from the other side of the end portion link member 111a to 113a and 111c to 113c is inserted in the throughhole 124 in the intermediate link member 111b to 113b through respective double row bearings 126.

Each of those bearings 126 is also employed in the form of, for example, a deep groove ball bearing and is made up of an outer ring 126a inserted into the throughhole 124 in the intermediate link member 111b to 113b, an inner ring 126b mounted externally on the shank portion 125 of the end link member 111a to 113a and 111c to 113c, and rolling elements 126c in the form of, for example, balls rollingly interposed between the outer ring 126a and the inner ring 126b. The bearing 126 for rotatably supporting the intermediate link member 111b to 113b relative to the end portion link member 111a to 113a and 111c to 113c is retained in position on by a retaining ring 127 so as not to separate from the intermediate link member 111b to 113b.

In each of the link mechanisms 111A to 113A (111B to 113B) as shown in FIG. 9 (FIG. 10), the angle and the length of the shaft member 120 and the geometric shape of the end link member 111a to 113a and 111c to 113c may be equal to each other on the fixing side and the input side (output side) and even the intermediate link member 111b to 113b have the fixing side and the input side (output side) that are similar in shape to each other. Also, the angular positional relation, relative to the plane of symmetry of the intermediate link member 111b to 113b, between the intermediate link member 111b to 113b and the end portion link member 111a to 113a and 111c to 113c that are connected with the fixing member 114A (114B) and the input member 115A (output member 115B) may be similar to each other on the fixing side and the input side (output side). In such a case, the fixing side group of the fixing member 114A (114B) and the end portion link member 111a to 113a and the input side (output side) group of the input member 115A (output member 115B) and the end portion member 111c to 113c will move in the same manner because of the geometrical symmetry and the fixing and input (output) side groups will rotate the same angle in the same manner at a constant speed. The plane of symmetry of the intermediate link member 111b to 113b when rotating at the constant speed is referred to as an isokinetic bisecting plane.

Because of the foregoing, when a plurality of the link mechanisms 111A to 113A (111B to 111B) of the same geometric shape having the fixing member 114A (114B) and the input member 115A (output member 115B) in common are arranged on a circumference, as the position at which those link mechanisms 111A to 113A (111B to 111B) can move with no ambiguity, the intermediate link members 111b to 113b is limited to the movement on the isokinetic bisecting plane and, hence, the isokinetic rotation can be obtained even when the fixing and input (output) side groups assume arbitrary working angles.

Each of the link mechanisms 111A to 113A (111B to 111B) has rotatable portions of the four revolve pairs comprised of a first joint portion between the end portion link member 111a to 113a and the fixing member 114A (114B), a second joint portion between the end portion link member 111c to 113c and the input member 115A (output member 115B), a third joint portion between the end portion link member 111a to 113a and the intermediate link members 111b to 113b, and a fourth joint portion between the end portion link member 111c to 113c and the intermediate link members 111b to 113b. Since these four rotatable portions are supported by means of bearings 119, 126, it is possible to reduce the rotational resistance, while the frictional resistance at those joint portions is suppressed, and hence, not only can a smooth power transmission be secured, but also the durability can be increased.

In this bearing structure, by applying a preload to the bearings 119, 126, a radial gap and a thrust gap are minimized to thereby suppress rattling at the joint portions and not only can the constant speed property be maintained with no phase difference between the fixing side and the input side (output side), but also generation of vibrations and noises can also be suppressed. In particular, by rendering the bearing gap of each of the bearings 119, 126 to be a negative gap, any backlash, which would occur between input and output, can be minimized.

According to the input side link actuating device 102A (output side link actuating device 102B) of the structure described hereinabove, the range of movement of the input member 115A (output member 115B) relative to the fixing member 114A (114B) can be made large. By way of example, the maximum bending angle defined between the center axis B of the fixing member 114A (114B) and the center axis C of the input member 115A (output member 115B) can be rendered to be about ±90°. Also, the angle of turn of the input member 115A (output member 115B) relative to the fixing member 114A (114B) can be made within the range of 0 to 360°.

Also, the input side link actuating device 102A (output side link actuating device 102B) of the structure described hereinabove is of a type, in which not only are the outer rings 119a of the bearings 119 capsulated within the fixing member 114A (114B) and the input member 115A (output member 115B), but also the inner rings 119b are connected with the end portion link members 111a to 113a and 111c to 113c, with the bearing structures embedded respectively within the fixing member 114A (114B) and the input member 115A (output member 115B), and, therefore, without unduly increasing the outer appearance of the whole, the outer appearance of the fixing member 114A (114B) and the input member 115A (output member 115B) can be enlarged. For this reason, it is easy to secure a fitting space in which the fixing member 114A (114B) is fitted to the fixing trestle 103, a fitting space in which the operating member 106 (FIGS. 6 and 7), as will be described later, is fitted to the input member 115A, and a fitting space in which a drive device (not shown) is fitted to the output member 115B.

As shown in FIGS. 6 and 7, the two input side gear members 121A, provided in the input side link actuating device 102A, and the two output side gear members 121B provided in the output side link actuating device 102B are meshed with each other. Those gear members 121A and 121B have the same number of teeth. A pair of the gear members 121A and 121B, that are meshed with each other, form a rotation transmitting mechanism 105. In other words, for one operating bench 50, two sets of the rotation transmitting mechanisms 105 are employed. By those two sets of the rotation transmitting mechanisms 105, respective rotations of the end link members 111a and 112a on the fixing side of the input side link mechanisms 111A and 112A are transmitted to the end link members 111a and 112a on the fixing side of the output side link mechanisms 111B and 112B. The reason that of the three sets of the input side link mechanisms 111A to 113A and the output side link mechanisms 111B to 113B the rotation transmitting mechanisms 105 are provided in the two sets thereof is because of the necessity for warranting the operation of the output side link actuating device 102B relative to the operation of the input side link actuating device 102A. It is, however, to be noted that all of the three sets of the input side link mechanisms 111A to 113B and the output side link mechanisms 111B to 113B may be provided with such a rotation transmitting mechanism 105.

The input member 115A of the input side link actuating device 102A has the operating member 106 fitted thereto for manual operation. Also, the output member 115B of the output side link actuating device 102B has the actuator main body 6 mounted thereon through the mounting carriage 57. The actuator main body 6 is identical in structure with that employed in the practice of the previously described embodiment. The fixing trestle 103 is fixedly mounted on a movable stage 107a of a direct acting unit 107.

When the input member 115A of the input side link actuating device 102A is moved by manipulating the operating member 106, the rotation of the end link members 111a and 112a on the fixing side of the input side link mechanisms 111A and 112A are transmitted to the end link members 111a and 112a on the fixing side of the output side link mechanisms 111B and 112B by the two sets of the rotation transmitting mechanisms 105, resulting in operation of the output member 115B of the output side link actuating device 102B. Since the input side link mechanisms 111A to 113A and the output side link mechanisms 111B to 113B are arranged in a mirror symmetrical relation with each other, the input member 115A and the output member 115B undergo respective motions that are mirror symmetrical to each other. For this reason, the manipulation of the operating member 106 and the operation of the actuator main body 6 mounted on the output member 115B coincide with each other and therefore, it is easy for the operator to accomplish a sensational operation.

Since the rotation transmitting mechanism 105 is so configured that the rotation can be transmitted from the end link member 111a and 112a on the fixing side of the input side link mechanism 111A and 112A to the end link member 111a and 112a on the fixing side of the output side link mechanism 111B and 112B through the engagement between the input side input gear member 121A and the output side gear member 121B, no slippage occurs within the rotation transmitting mechanism 105 and the rotation can be assuredly transmitted. Since the number of teeth of the input side gear member 121A and the number of teeth of the output side gear member 121B are the same, the number of rotations of the end link member 111a and 112a on the fixing side of the input side link mechanism 111A and 112A and that of the end link member 111a and 112a on the fixing side of the output side link mechanism 111B and 112B become equal to each other and, therefore, the same movement can be transmitted from the input side link actuating device 102A to the output side actuating device 102B.

Figure 12:
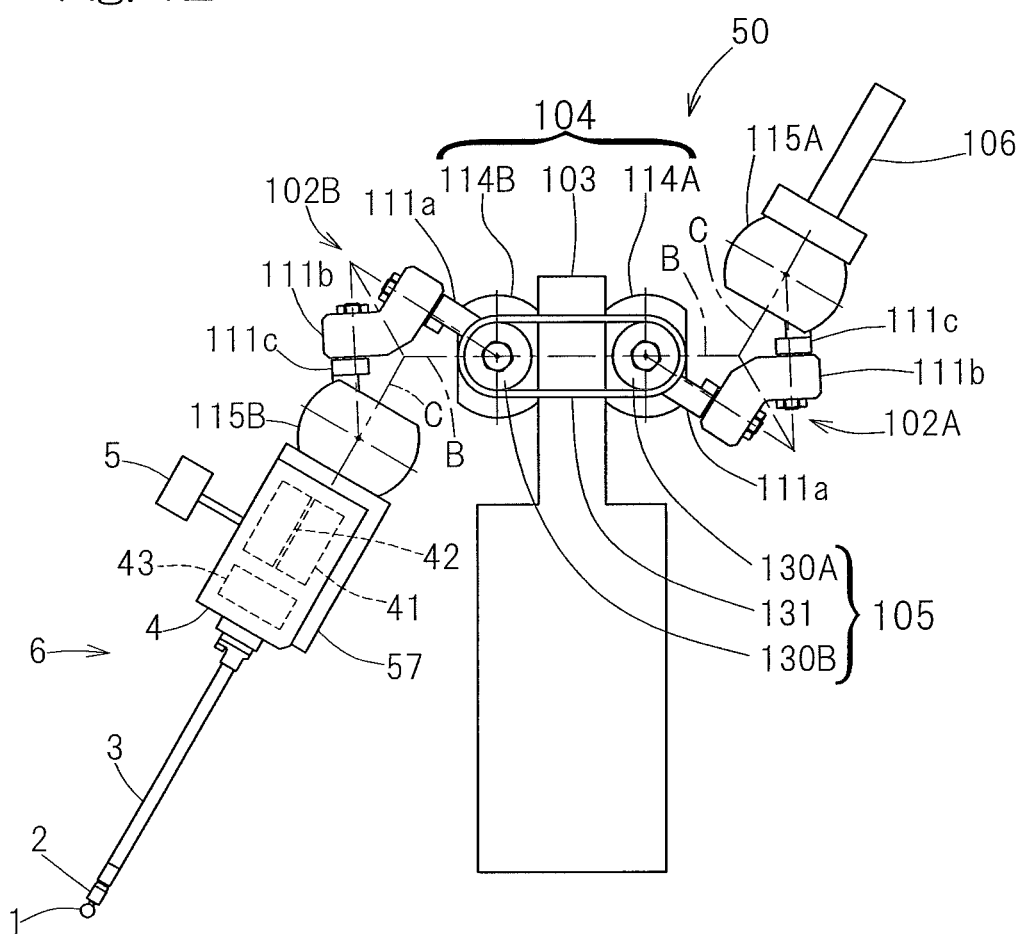
FIG. 12 is a front elevational view, with a portion removed, showing the remote controlled actuator assembly according to a fourth preferred embodiment of the present invention.

FIG. 12 illustrates a fourth preferred embodiment of the present invention. The operating bench 50 employed in the practice of this embodiment is rendered to be of a type in which the rotation transmitting mechanism 105 is employed in the form of a belt transmission mechanism. The input side link actuating device 102A and the output side link actuating device 102B are of the same shape and the same dimension and are fixedly arranged so as to assume a rotational symmetry with respect to the fixing trestle 103. Of the three shaft members 120 provided in each of the fixing members 114 and 114B, the two shaft members 120, including the shaft member 120 with which the end link members 111a are connected, are provided with respective pulleys 130A and 130B of the same diameter in place of the use of the gear members 121A and 121B employed in the practice of the previously described embodiments, and a transmission belt 131 is trained between those pulleys 130A and 130B. The pulleys 130A and 130B referred to above and the transmission belt 131 also referred to altogether form the rotation transmitting mechanism 105. The transmission belt 131 is preferably employed in the form of a serrated timing belt. In the case of this embodiment, the fixing trestle 103 is, for example, fixed and disposed on a fixed structure.

According to this construction described above, the number of rotations of the end link member 111a on the fixing side of the input side link mechanism 111A, and that of the end link member 111a on the fixing side of the output side link mechanism 111B are equal to each other, and the same motion is therefore transmitted from the input side link actuating device 102A to the output side link actuating device 102B. Since the input side link mechanism 111A to 113A and the output side link mechanism 111B to 113B are arranged in a rotation symmetrical relation to each other, the operation of the input side link actuating device 102A and that of the output side link actuating device 102B are in a rotation symmetrical relation to each other. In other words, the actuator main body 6 moves in a direction counter to an operating direction of the operating member 106, and therefore, the feeling that the actuator main body 6 is operated about the fixing trestle 103 as a fulcrum can be obtained. Thus, in this embodiment, the operation of the operating member 106 and the operation of the actuator main body 6 are reverse to each other. Depending on the type of the actuator main body 6 and the situation in which the actuator main body 6 is used, it may often occur that this reverse operation mode is considered more favorable in terms of operability than the normal operation mode in which the operation of the operating member 106 and the operation of the actuator main body 6 are the same, and, accordingly, the employment of the structure designed in accordance with this embodiment is highly advisable.

Figure 13:
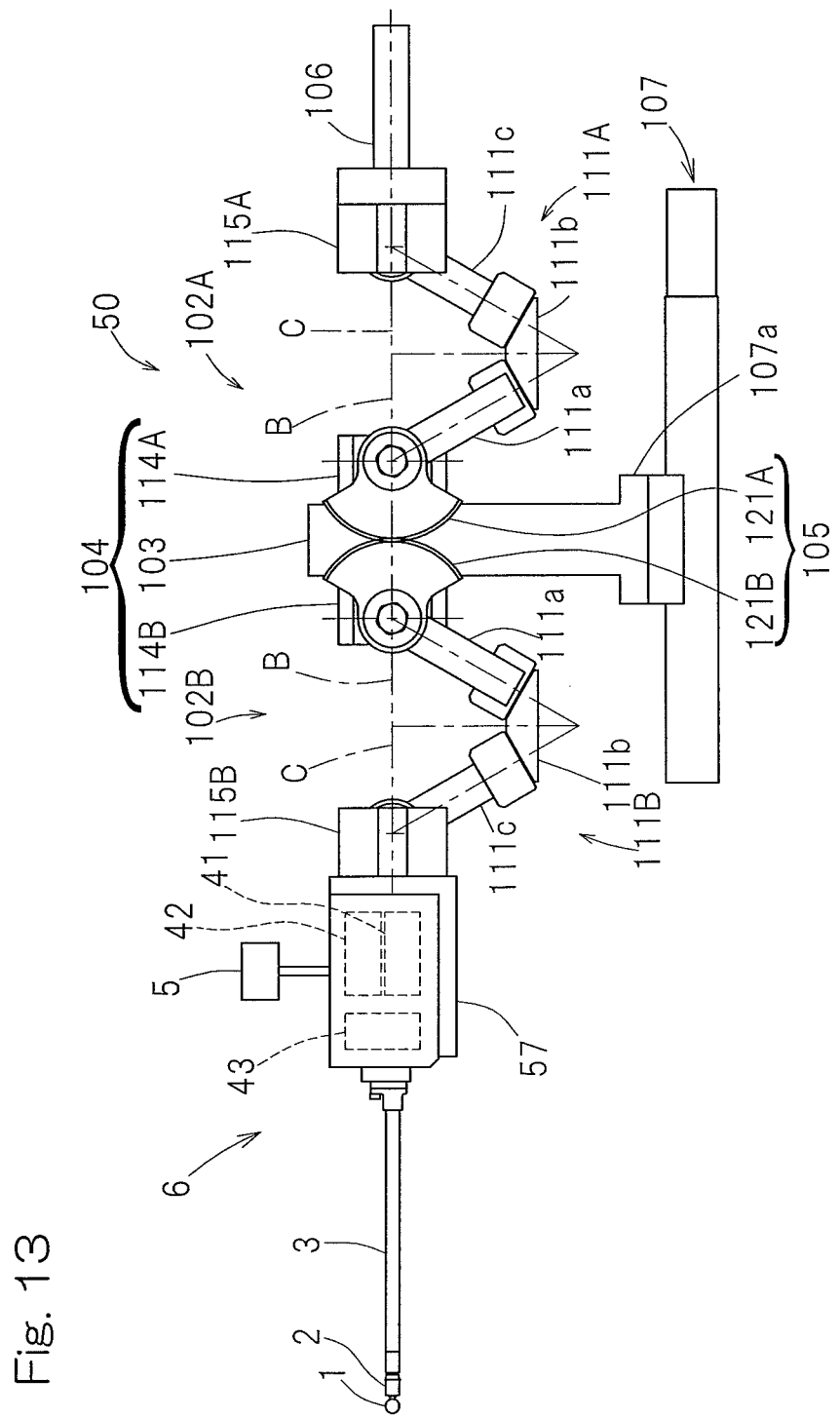
FIG. 13 is a front elevational view, with a portion removed, showing the remote controlled actuator assembly according to a fifth preferred embodiment of the present invention.
Figure 14B:
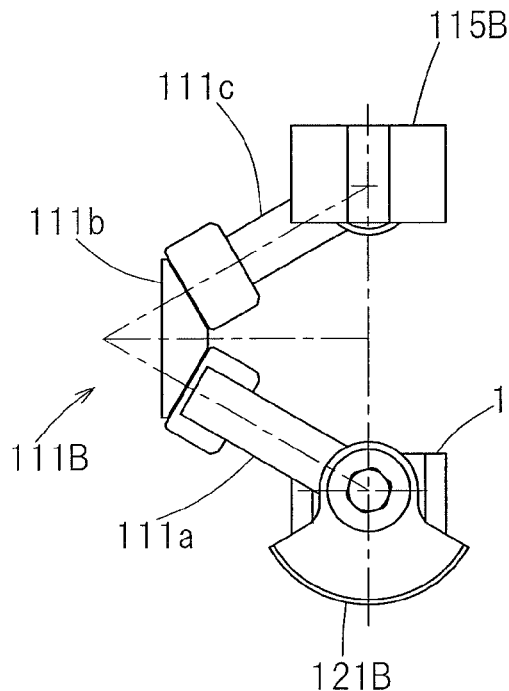
FIG. 14B is a front elevational view, with a portion removed, showing the output side link actuating device employed in the remote controlled actuator assembly of FIG. 13.
Figure 14A:
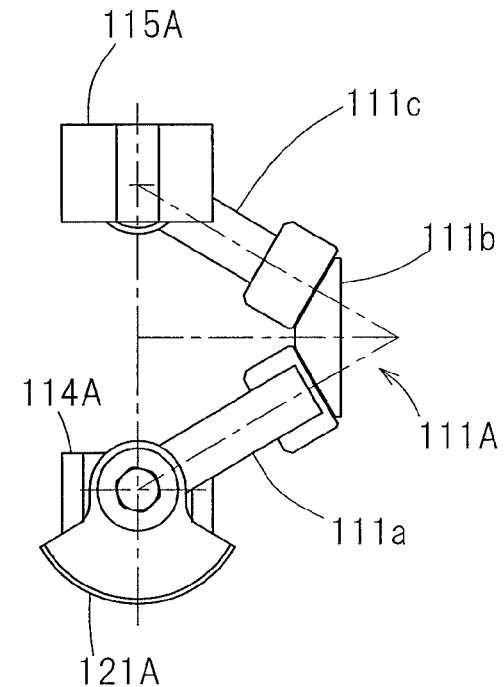
FIG. 14A is a front elevational view, with a portion removed, showing the input side link actuating device employed in the remote controlled actuator assembly of FIG. 13.
Figure 15:
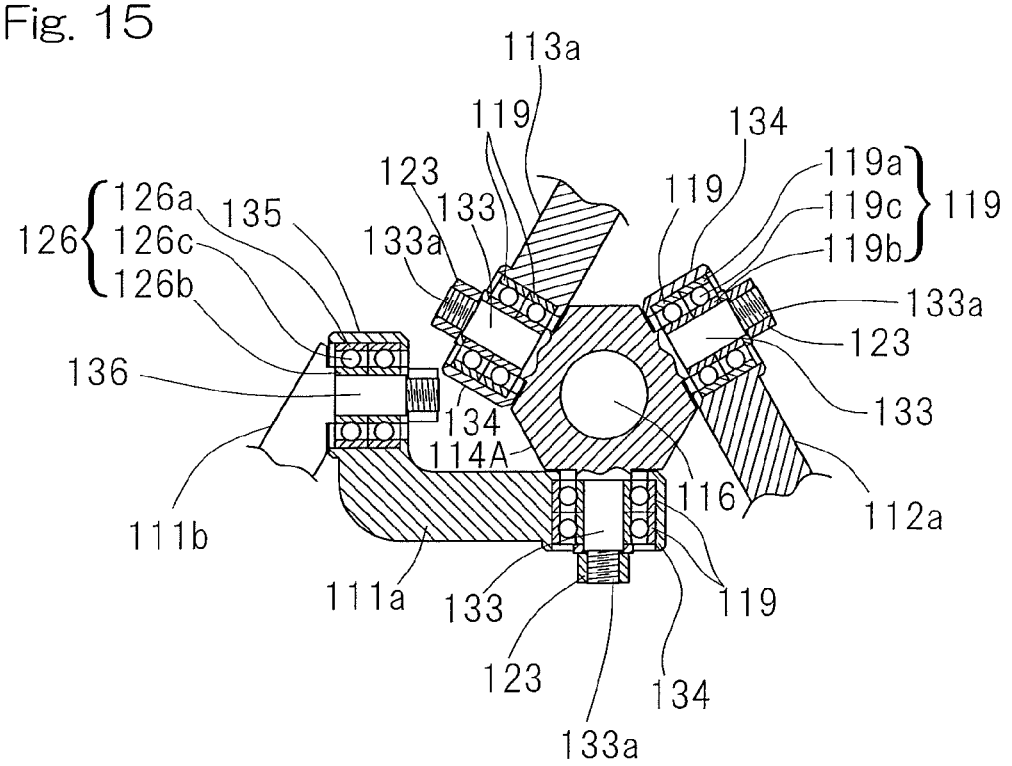
FIG. 15 is a longitudinal sectional view showing the fixing member, the end link member on the fixing side and the intermediate link member of the input side link actuating device.

FIGS. 13 to 15 illustrate a fifth preferred embodiment of the present invention. The operating bench 50 employed in the practice of this fifth embodiment is such that the bearings 119 (best shown in FIG. 15) used to support the end link members 111a to 113a and 111c to 113c relative to the fixing members 114A, 114B and the input and output members 115A, 115B, respectively are rendered to be of an outer ring rotating type. In other words, in this embodiment, bearings of an outer ring rotating type are employed for the bearings 119. To describe the connection between the fixing member 114A of the input side link actuating device 102A and the end link member 111a to 113a on the fixing side as an example, as best shown in FIG. 15, a shank portion 133 is formed at three circumferential locations of the fixing member 114A, the inner rings 119b of the bearings 119 of double row are mounted on the shank portion 133, and the outer rings 119a of the bearings 119 are received in a corresponding bearing support portion 134 formed in the end link member 111a to 113a. In other words, it is the structure in which the inner rings 119b are fixed to the fixing member 114A and the outer rings 119a are rotatable together with the end link member 111a to 113a. With a nut 123 threadingly fastened to a front end threaded portion 133a of each shank portion 133, a predetermined amount of preload is applied to the respective bearing 119. The connection between the fixing member 114B and the end link member 111a to 113a on the fixing side, the connection between the input member 115A and the end link member 111c to 113c on the input side, and the connection between the output member 115B and the end link member 111c to 113c on the output side are each similar in construction to that described above.

Of the three end link members 111a to 113a on the fixing side, the two end link members including the end link member 111a are formed integrally with the input side gear members 121A (as shown in FIGS. 13 and 14A). Also, the connection between the fixing member 114B of the output side link actuating device 102B and the end link member 111a to 113a on the fixing side is formed integrally with the output gear member 121B (as shown in FIGS. 13 and 14B). The pair of those gear members 121A and 121B altogether form the rotation transmitting mechanism 105. It is, however, to be noted that the gear members 121A and 121B may be members separate from the end link members 111a and may then be fixed to the end link members 111a by means of fixing elements.

In addition, in the instance as shown, the bearing 126 for supporting the intermediate link member 111b relative to the end link member 111a on the fixing side is such that the outer ring 126a is received within a bearing support portion 135 of the end link member 111a while the inner ring 126b is mounted on a shank portion 133 of the intermediate link member 111b. Each of the connections between the end link members 111c on the input and output sides and the intermediate link member 111b is of a structure similar to that described above. The fixing member 114A and 114B, the input member 115A and the output member 115B are formed with respective throughholes 116 extending in the axial direction at a center portion thereof, as is the case with those in the previously described third embodiment.

Figure 16:
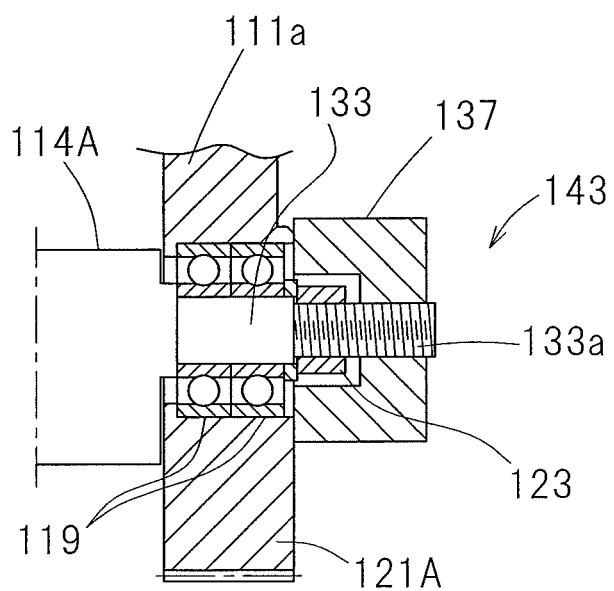
FIG. 16 is a schematic longitudinal sectional view showing a connection between the fixing member, provided with one example of a freezing mechanism, and the end link member on the fixing side.
Figure 17A:
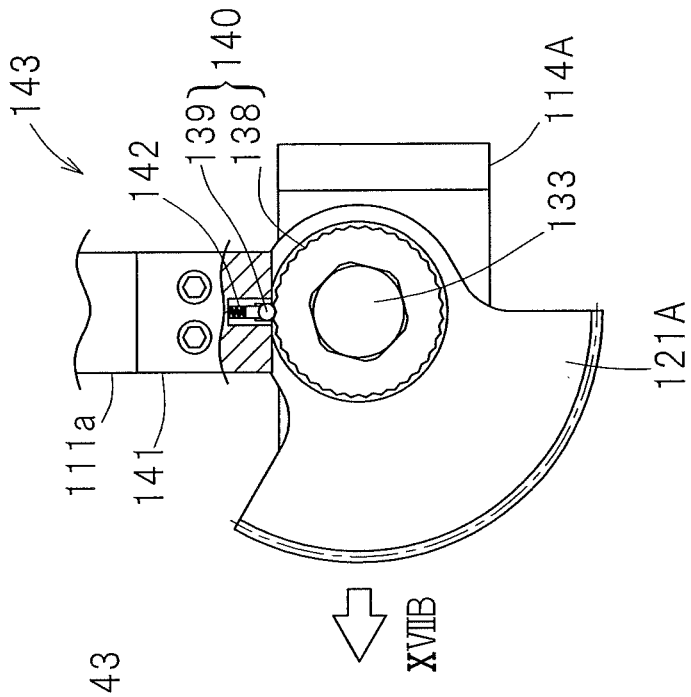
FIG. 17A is a longitudinal sectional view showing the connection between the fixing member, provided with a different example of the freezing mechanism, and the end link member on the fixing side.
Figure 17B:
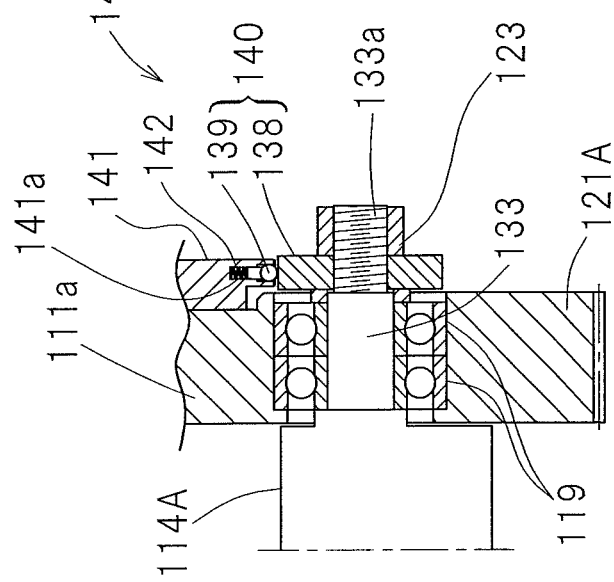
FIG. 17B is a diagram showing the connection, shown in FIG. 17A, as viewed from a direction indicated by XVIIB in FIG. 17A.
Figure 18:
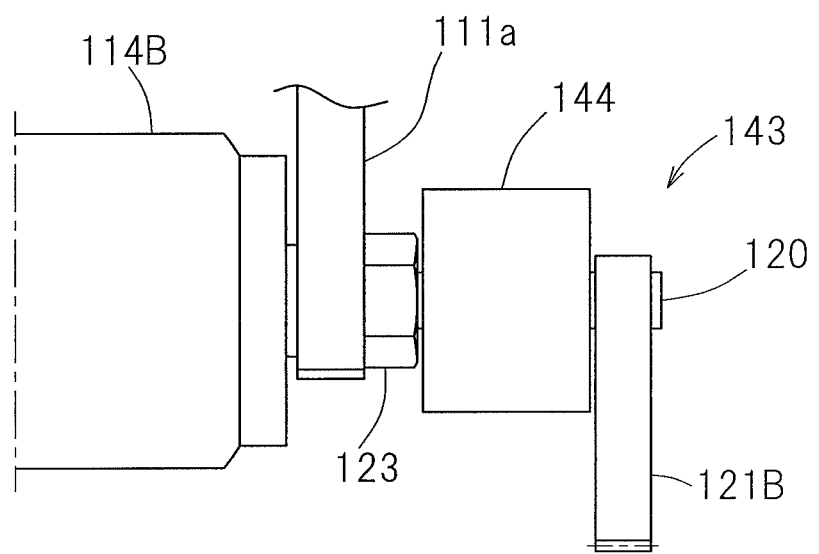
FIG. 18 is a diagram showing an appearance of the connection between the fixing member, provided with a further different example of the freezing mechanism, and the end link member on the fixing side.

As shown in FIGS. 16 to 18, the operating bench 50 may be provided with a freezing mechanism for positioning the input and output side link actuating devices 102A and 102B in arbitrary attitudes. The freezing mechanism 143 shown in FIG. 16 is provided in the input side link actuating device 102A (shown in FIGS. 13 to 15), in which the outer ring rotating type bearing 119 supports the end link member 111a on the fixing side relative to the fixing member 114A. In this example, a freezing member 137 is threaded to the shank portion 133 of the fixing member 114A so as to contact a side face of the end link member 111a. Accordingly, by the effect of a frictional force developed between the end link member 111a and the freezing member 137, the degree of freedom of rotation of the end link member 111a is suppressed. If such freezing member 137 is provided in two or more of three end link members 111a to 113a, the movements of the link actuating device 102A and 102B are suppressed and it is possible to fix the link actuating device 102A and 102B in the arbitrary attitude. It is, however, to be noted that the freezing member 137 may be provided in the output side link actuating device 102B. Also, it may be provided in the revolve pair of the input side or output side end link member (not shown). In either case, functions and effects similar to those described above can be obtained.

The freezing mechanism 143 shown in FIGS. 17A and 17B, too, is provided in the input side link actuating device 102 (shown in FIG. 15) having the outer ring rotating type bearing 119 and a gear 138, fitted to the shank portion 133 of the fixing member 114A, and a stopper 139 engageable with the gear 138 altogether constitute a rotation constraining unit 140. The stopper 139 is retained within a stopper holding hole 141a, defined in a fitting member 141 that is fixed to the end link member 111a, and is biased by a spring 142 towards a center side of the shank portion 133 with its spherical front end portion consequently contacting an outer peripheral surface of the gear 138. With the front end portion of the stopper 139 engaged in a groove of the gear 138, the degree of freedom of rotation of the end link member 111a is suppressed. If such rotation constraining unit 140 is provided in two or more of the three end link members 111a to 113a, respective movements of the link actuating devices 102A and 102B are suppressed and it is possible to fix the link actuating devices 102A and 102B in the arbitrary attitudes. This rotation constraining unit 140 referred to above may, however, be provided in the output side link actuating device 102B. Also, it may be provided in the revolve pair of the input side or output side end link member (not shown). In either case, functions and effects similar to those described hereinbefore can be obtained.

The freezing mechanism 143 shown in FIG. 18 is provided in the output side link actuating device 102B (shown in FIG. 11), in which the inner ring rotating type bearings 119 support the end link member 111a on the fixing side relative to the fixing member 114B. In this example, one way clutch 144 is interposed between the revolve pair of the end link member 111a on the fixing side and the gear member 121B forming the rotation transmitting mechanism 105. The one way clutch 144 is operable to transmit the rotation from the rotation transmitting mechanism 105, but to lock the transmission of the input from the end link member 111a. Accordingly, even when a force acts on the output side link actuating device 102B, no rotational force is transmitted to the input side link actuating device 102A, and therefore, the link actuating device 102A and 102B are retained in the attitude as it stands. In other words, even when an external force acts on the output member 115B and the actuator main body 6 mounted on such output member 116B, the operation will not be disturbed and is therefore safe.

Figure 19:
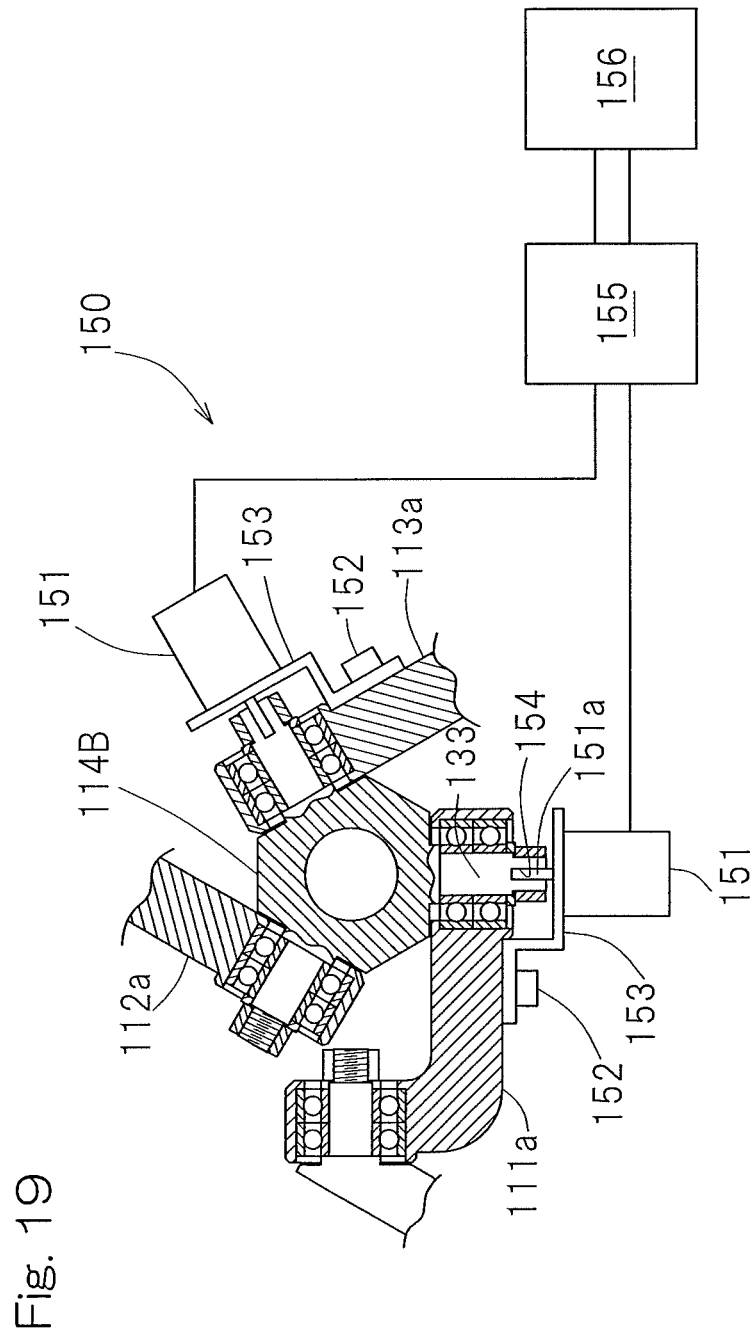
FIG. 19 is a schematic structural diagram showing an attitude detecting mechanism added to the longitudinal sectional view showing the fixing member, the end link member on the fixing side and the intermediate link member of the output side link actuating device.

FIG. 19 illustrates a schematic structural diagram of an attitude detecting mechanism 150 for detecting the attitude of the link actuating device 102A and 102B. This attitude detecting mechanism 150 includes a rotational angle detector 151 provided in two or more of the three end link members 111A to 113a on the fixing side of the output side link actuating device 102B. In the instance as shown, the two rotational angle detectors 151 detect the rotational angle of the respective end link members 111a and 113a on the fixing side. By way of example, the rotational angle detector 151 is employed in the form of a rotary encoder and is installed on a fitting member 153 fixed to the fixing member 114B by means of a bolt 152. A rotary shaft 151a of the rotational angle detector 151, which is the rotary encoder, is fixedly inserted into a hole 154 defined in the shank portion 133 of the fixing member 114B.

Figure 20:
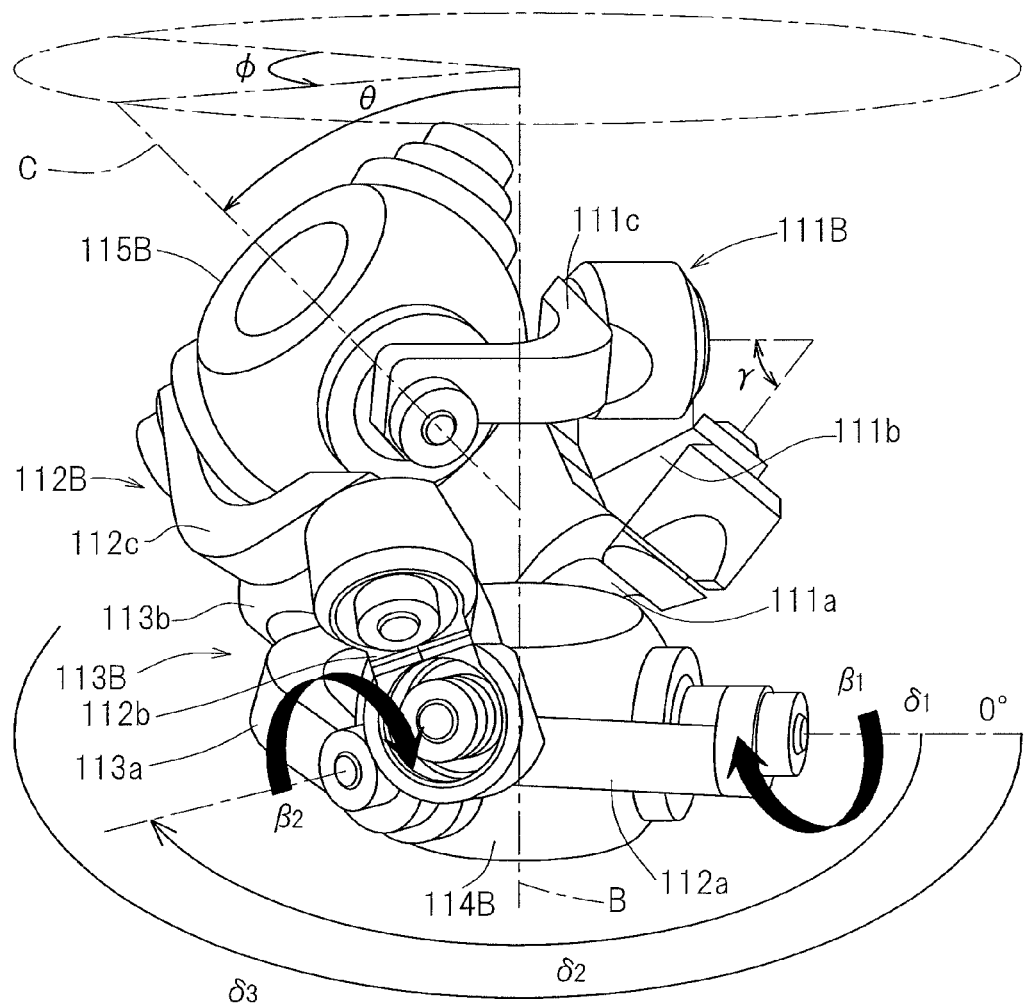
FIG. 20 is a perspective view showing angles of various portions of the output side link actuating device.

Respective output signals of the two rotational angle detectors 151 referred to above are fed to an angle calculator 155. The angle calculator 155 is operable to calculate from the above described output signals the bend angle θ (FIG. 20) and the angle of traverse φ (FIG. 20), both descriptive of the attitude of the link actuating device 102A and 102B. The bend angle θ means a vertical angle with the input member 115A (the output member 115B) inclined relative to the center axis B of the fixing member 114A (114B) whereas the angle of traverse φ means a horizontal angle with the input member 115A (the output member 115B) inclined relative to the center axis B of the fixing member 114A (114B). The calculated bend angle θ and the calculated angle of traverse φ are displayed by an angle display unit 156. The use of the attitude detecting mechanism 150 of the structure hereinabove described is effective to allow the operating bench 50 to be operated while looking at the attitude of the link actuating devices 102A and 102B displayed on the angle display unit 156 and, accordingly, the operability increases.

The calculation of the bend angle θ and the angle of traverse φ is accomplished by the angle calculator 155 is carried by means of a forward transform using the following relational equation. The forward transform means a conversion to calculate the bend angle θ and the angle of traverse φ from the rotational angle of the end link member 111a to 113a;

$$\cos(\theta/2)\sin\beta n - \sin(\theta/2)\sin(\phi+\delta n)\cos\beta n + \sin(\gamma/2) = 0$$

wherein βn (β1 and β2 indicated in FIG. 20) stands for the rotational angle in a connecting end of the end link member 111a to 113a on the fixing side that is rotatably connected with the fixing member 114B; γ (indicated in FIG. 20) stands for the angle formed between a connecting end axis of the intermediate link member 111b to 113b, which is rotatably connected with the end link member 111a on the fixing side, and a connecting end axis of the intermediate link member 111b to 113b which is rotatably connected with the end link member 111c to 113c on the output side; and δn (δ1, δ2 and δ3 indicated in FIG. 20) stands for the angle of separation in a circumferential direction of the respective end link member 111a to 113a on the fixing side relative to the end link member 111a on the fixing side which becomes a reference.

Figure 21:
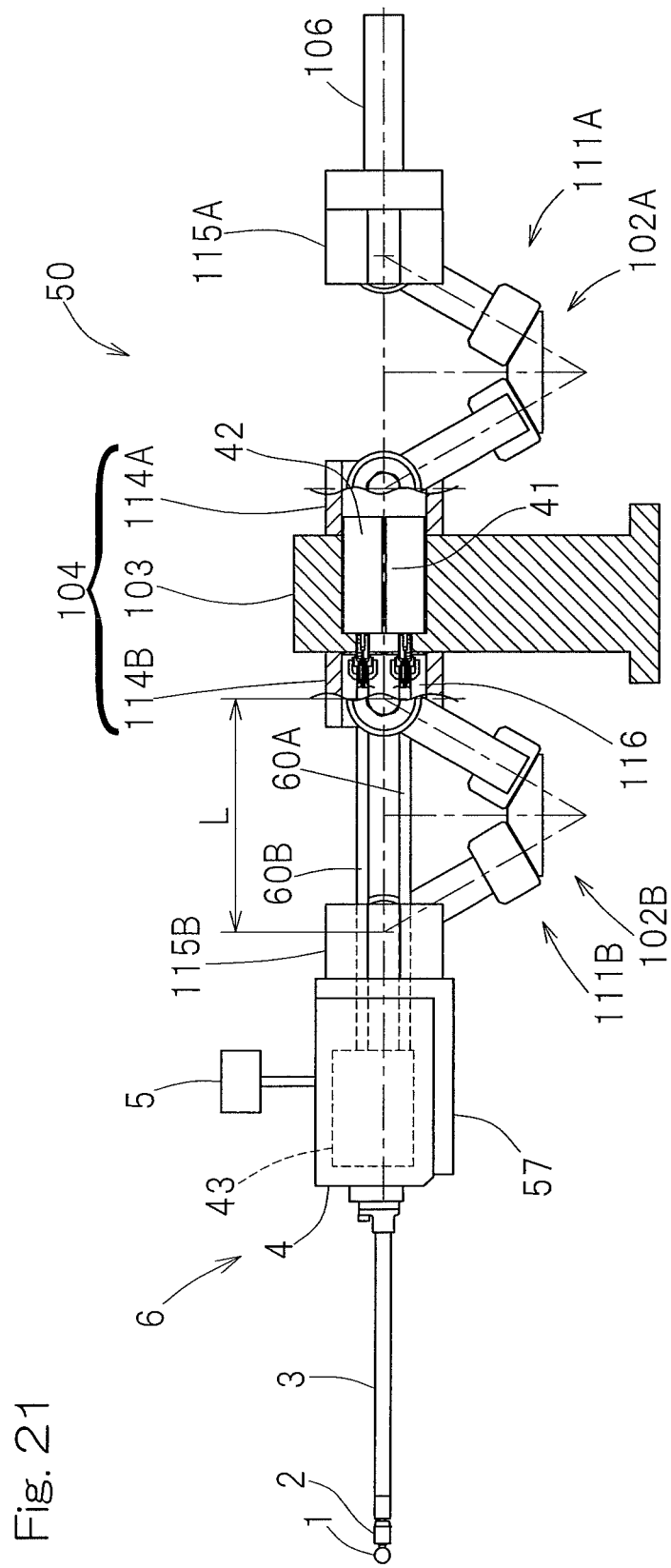
FIG. 21 is a front elevational view, with a portion removed, showing the remote controlled actuator assembly according to a sixth preferred embodiment of the present invention.

FIG. 21 illustrates a sixth preferred embodiment of the present invention. The remote controlled actuator assembly according to this sixth embodiment is such that the tool rotation drive source 41 and the attitude altering drive source 42, both being sources of rotation, are mounted on the fixing trestle 103 of the operating bench 50 so that the respective rotational forces of the drive sources 41 and 42 can be transmitted to the actuator main body 6 by means of a flexible tool rotating wire 60A and a flexible attitude altering wire 60B. Each of the flexible wires 60A and 60B is provided having been inserted into the respective throughhole 116 in the fixing member 114B and the output member 115B of the output side link actuating device 102B. The details of those flexible wires 60A and 60B will be described later.

Mounting of the tool rotation drive source 41 and the attitude altering drive source 42 on the operating bench 50 in the manner described hereinabove makes it possible to reduce the weight of the actuator main body 6, accompanied by an increase of the operability. Since the flexible wires 60A and 60B for transmitting the respective rotations of the tool rotation drive source 41 and the attitude altering drive source 42 to the actuator main body 6 have a flexibility, the respective rotations of the tool rotation drive source 41 and the attitude altering drive source 42 can be assuredly transmitted to the actuator main body 6 even though the attitude of the output side link actuating device 102B is altered. Since the distance L between a spherical link center on the fixing side and that on the output side does not change even though the attitude of each of the link mechanisms 111B to 113B is altered, there is no risk that a large axial force (a pulling force) may act on the flexible wires 60A and 60B. Also, since the flexible wires 60A and 60B are provided having been inserted in the respective throughholes 116 in the fixing member 114B and the output member 115B, wiring is each to accomplish and there is no possibility that it may constitute a cause of disturbance.

It is to be noted that only one of the tool rotation drive source 41 and the attitude altering drive source 42 may be mounted on the fixing trestle 103. In such case, only one of the flexible tool rotating wire 60A and the flexible attitude altering wire 60B has to be provided having been inserted in the respective throughholes 116 of the fixing member 114B and the output member 115B of the output side link actuating device 102B.

Figure 22A:
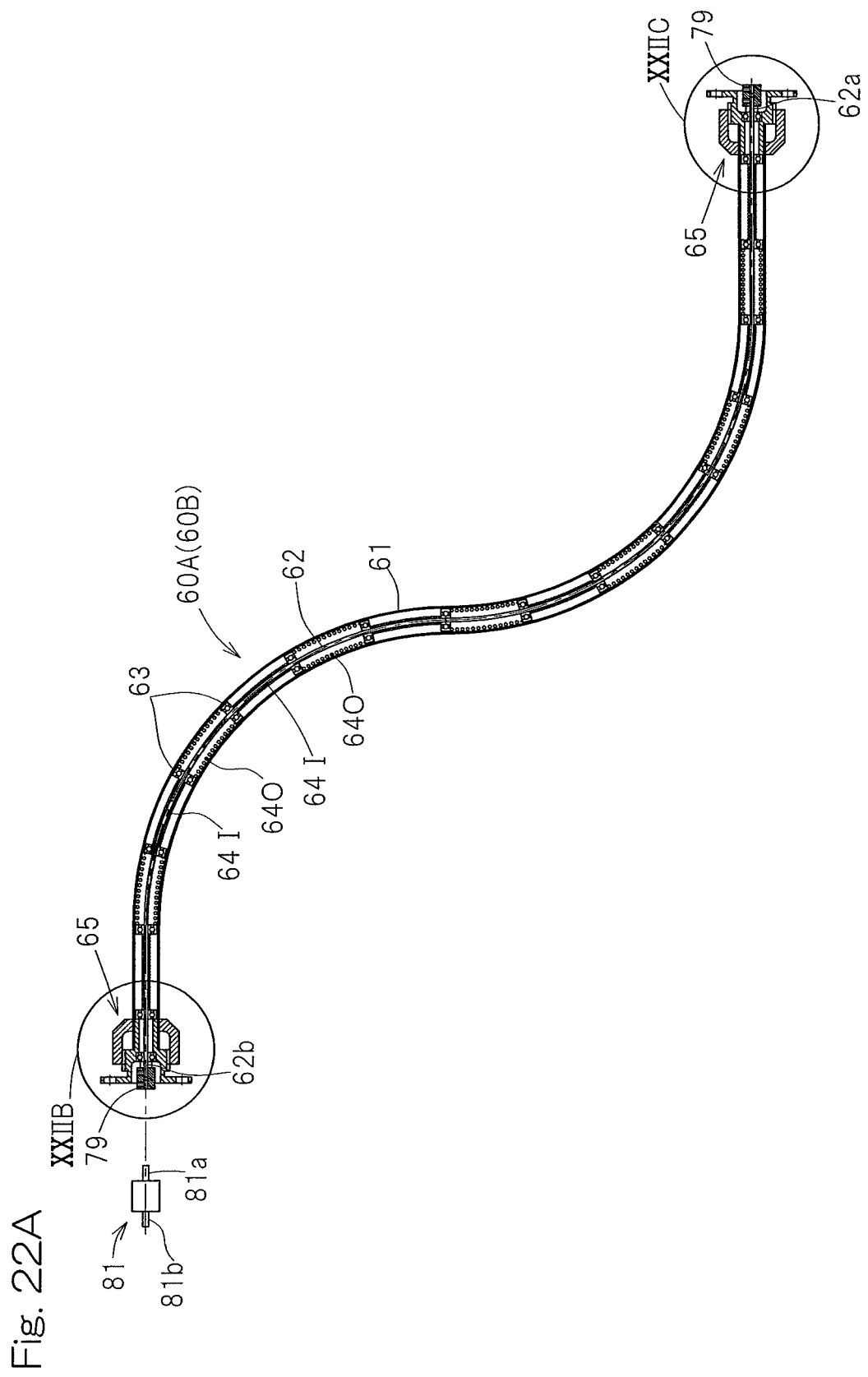
FIG. 22A is a longitudinal sectional view showing a flexible wire employed in the remote controlled actuator assembly.

One example of the structure of the flexible wire 60A and 60B is shown in FIGS. 22A to 22C. The flexible wire 60A (60B) includes a flexible outer tube 61, a flexible inner wire 62 provided at a center position within the outer tube 61, and a plurality of rolling bearings 63 for rotatably supporting the inner wire 62 relative to the outer tube 61. The inner wire 62 has its opposite ends which will become an input end 62a and an output end 62b for rotation, respectively. The outer tube 61 is made of, for example, a resinous material. For the inner wire 62, a wire made of, for example, metal, resin or glass fibers is employed. The wire may be in the form of a single wire or a twisted wire.

The rolling bearings 63 are disposed along a center line of the outer tube 61 and spaced a distance from each other, and spring elements 64I and 64O for applying respective preloads to those rolling bearings 63 are provided between the neighboring rolling bearings 63. The spring elements 64I and 64O are in the form of, for example, compression coils and are provided as if a winding wire is wound around an outer periphery of the inner wire 62. The spring elements includes an inner ring spring element 64I for generating the preload in the inner ring of the rolling bearing 63 and an outer ring spring element 64O for generating the preload in the outer ring, and they are arranged alternately.

The outer tube 61 has its opposite ends each provided with a coupling member 65 for connecting the outer tube 61 with members to be coupled. The coupling member 65 is made up of a male threaded member 66 and a female threaded member 73.

The male threaded member 66 is in the form of a tubular member having an inner periphery formed with a throughhole 67 and is formed with a male threaded portion 68 in an outer periphery thereof at an intermediate location in an axial direction thereof. One end, i.e., a first end, of the male threaded member 66 in the axial direction is provided with an axially extending cylindrical portion 69. The outer diameter of this cylindrical portion 69 is so chosen as to be a value enough to be press-fitted to an inner diameter portion of the outer tube 61. Also, the opposite end, i.e., a second end, of the male threaded member 66 in the axial direction is provided with a radially outwardly extending flange portion 70. This flange portion 70 forms a connecting unit for connecting it with the member to be coupled and has a plurality of circumferential portions formed with respective insertion holes 71 for the insertion of fixing members such as, for example, bolts therethrough. The throughhole 67 referred to previously has its inner diameter decreasing so stepwise as to define a small diameter portion 67a, an intermediate diameter portion 67b and a large diameter portion 67c in this order from the side of the cylindrical portion 69 towards the side of the flange portion 70. The intermediate diameter portion 67b has a rolling bearing 72 inserted thereinto for rotatably supporting the inner wire 62.

On the other hand, the female threaded member 73 is in the form of a tubular member having a cylindrical portion 74 and a collar shaped portion 75 extending from one end of the cylindrical portion 74 in a direction radially inwardly thereof, and a female threaded portion 76 engageable with the male threaded portion 68 of the male threaded member 66 is formed on an inner peripheral of a tip end portion of the cylindrical portion 74. The collar shaped portion 75 has an inner diameter so chosen as to be press-fitted to the outer periphery of the outer tube 61.

In order to connect the outer tube 61 with the member to be coupled, the cylindrical portion 69 of the male threaded member 66 is first engaged in an inner diameter portion of the outer tube 61, and the collar shaped portion 75 of the female threaded member 73 is then engaged with an outer diameter portion of the outer tube 61 and, starting from this condition, the male threaded portion 68 of the male threaded member 66 and the female threaded portion 76 of the female threaded member 73 are engaged with each other. By so doing, the cylindrical portion 69 of the male threaded member 66 cooperates with the collar shaped portion 75 of the female threaded member 73 to fixedly sandwich one end of the outer tube 61 from inside and outside. The inner wire 62 is passed through the throughhole 67 of the male threaded member 66 and is supported by the rolling bearing 72 inserted into the intermediate diameter portion 67b of the throughhole 67. Thereafter, the flange portion 70 of the male threaded member 66 is connected with the member to be coupled. This connection is accomplished by a fixing member (not shown) such as, for example, a bolt inserted through the insertion hole 71. In this way, the connection between the outer tube 61 and the member to be coupled completes and the condition as shown in FIGS. 22B and 22C establishes.

Starting from this condition, when the male threaded portion 68 is disengaged from the female threaded portion 76, the outer tube 61 is released from the restraint then accomplished by the cylindrical portion 69 of the male threaded portion 66 and the collar shaped portion 75 of the female threaded member 73 and, hence, the connection between the outer tube 61 and the member to be coupled is disconnected. Connecting and disconnecting procedures between the outer tube 61 and the member to be coupled are easy to perform.

Also, starting from the condition in which the outer tube 61 and the coupling member 65 are connected together, the connecting and disconnecting procedures between the flexible wire 60A (60B) and the member to be coupled may be performed by means of a connecting unit (flange portion 70) of the male threaded member 66. Yet, the connecting and disconnecting procedures between the flexible wire 60A (60B) and the member to be coupled become easy to perform.

The input and output ends 62a and 62b of the inner wire 62 referred are each provided with a coupling 79 for connection with a rotary shaft. In the case of the flexible tool rotating wire 60A, the input end 62a of the inner wire 62 is connected with the output shaft of the tool rotation drive source 41, and the output end 62b of the inner wire 62 is connected with a base end of the rotary shaft 22, defined in the actuator main body 6. In the case of the flexible attitude altering wire 60B, the input end 62a of the inner wire 62 is connected with an output shaft of the attitude altering drive source 42, and the output end 62b of the inner wire 62 is connected with an input shaft 81a of a reduction gear 81 as will be detailed later. In the description that follows, the output shaft of the tool rotation drive source 41, the rotary shaft 22, the output shaft of the attitude altering drive source 42 and the input shaft 81a of the reduction gear 81 are collectively referred to as the rotary shaft 78.

The coupling 79 in the illustrated instance has a throughhole 79a extending in a direction axially thereof, and an axially spaced, two threaded holes 79b are provided as radially extending between this throughhole 79a and an outer periphery surface. The inner wire 62 and the rotary shaft 78 are inserted into the throughhole 79a from both sides thereof, and a tip of a threaded member (not shown) such as, for example, a bolt threadingly engaged within the threaded hole 79b is held in contact with the inner wire 62 and the rotary shaft 78 to urge the latter to thereby connect the inner wire 62 and the rotary shaft 78 together.

Since the flexible wire 60A (60B) of the structure described above is such that the spring elements 64I and 64O for applying the preloads to the rolling bearings 63 are provided between the neighboring rolling bearings 63, it is possible to prevent the natural frequency of the inner wire 62 from lowering, and the inner wire 62 can be therefore rotated at a high speed. Since the inner ring spring element 64I and the outer ring spring element 64O are alternately arranged in the direction lengthwise of the inner wire 62, the spring elements 64I and 64O can be provided without the outer tube 61 being unduly increased in its diameter.

FIGS. 23A and 23B illustrate an interior structure of the main body base end housing 4 for the remote controlled actuator assembly of the type shown in FIG. 21. As shown therein, the rotary shaft 22 is provided within the main body base end housing 4 so as to extend leftwards and rightwards, and the base end of the rotary shaft 22 is connected with the inner wire 62 of the flexible tool rotating wire 60A through the coupling 79. Accordingly, the rotation of the tool rotation drive source 41 (shown in FIG. 21) is transmitted to the rotary shaft 22. Also, the main body base end housing 4 is provided with the attitude altering drive mechanism 43. The attitude altering drive mechanism 43 includes the reduction gear 81 for reducing and then outputting the rotation of the attitude altering drive source 42 (shown in FIG. 21), that is transmitted by the flexible attitude altering wire 60B, and a motion converter mechanism 43c for converting the rotary motion of the reduction gear 81 into a linear reciprocating motion.

The motion converter mechanism 43c has a ball screw mechanism 84. The ball screw mechanism 84 includes a screw shaft 84a and a nut 84b that is in threaded engagement with the screw shaft 84a through a ball (not shown). The screw shaft 84a has a first end and a second end opposite to the first end, with the first and second ends being supported by respective bearings 82 and with the first end connecting, via a coupling 83, to the output shaft 81b of the reduction gear 81. The linear motion member 86 described above is fixed to the nut 84b, with the linear motion member 86 being guided by a linear guide 85 such that the linear motion member 86 is moveable axially of the screw shaft 84a. A tip end face of the linear motion member 86 forms a contact portion 86a that contacts a base end of the attitude altering member 31.

Rotation of the output shaft 81b of the reduction gear 81 is converted by the ball screw mechanism 84 to a linear motion that makes the linear motion member 86 move in a linear fashion along the linear guide 85. The movement of the linear motion member 86 to the left side of FIG. 23A pushes the attitude altering member 31, causing the attitude altering member 31 to advance. On the other hand, the movement of the linear motion member 86 to the right side of FIG. 23A causes the attitude altering member 31 to retract, due to the push back caused by the elastic repulsion force of the aforementioned restoring elastic member 32.

The linear motion member 86 is associated with a linear scale 87a whose scale is read by a linear encoder 87b fixed to the main body base end housing 4. These linear scale 87a and linear encoder 87b form a position detector 87 that is operable to detect an advance or retraction position of the attitude altering member 31. In particular, the output of the linear encoder 87b is transmitted to an advance or retraction position estimator 88 which is configured to estimate an advance or retraction position of the attitude altering member 31. In other words, the position detector 87 is operable to detect an operational position of a power transmission member—formed by the linear motion member 86—which is arranged between the reduction gear 81 and the attitude altering member 31, and the result of the detection is used to estimate an advance or retraction position of the attitude altering member 31.

The advance or retraction position estimator 88 includes a relation setting means (not shown), in which the relationship between an advance or retraction position of the attitude altering member 31 and an output signal of the linear encoder 87b is set in terms of an arithmetic equation or table. The advance or retraction position estimator 88 uses the relation setting means to estimate, from a received output signal, an advance or retraction position of the attitude altering member 31. The advance or retraction position estimator 88 may be included in the controller 5 (FIG. 21), or may be included in an external control device. The controller 5 controls the attitude altering drive source 42 based on a detection value of the advance or retraction position estimator 88.

The rotation of the attitude altering drive source 42 is transmitted to the reduction gear 81 via the inner wire 62 of the flexible attitude altering wire 60B, and then the speed of that rotation is reduced by the reduction gear 81. Further, the rotational motion of the output shaft 81b of the reduction gear 81 is converted by the motion converter mechanism 43c to reciprocation motion for transmission to the linear motion member 86 which forms the final output member. The advance or retraction of the linear motion member 86 is transmitted, via the contact portion 86a, to the base end of the attitude altering member 31, thereby causing the attitude altering member 31 to advance or retract. With the provision of the reduction gear 81, even a possibly low output torque from the attitude altering drive source 42 can generate a large torque at an output of the reduction gear 81 thereby to impart a great acting force on the linear motion member 86. This ensures that the advance or retraction of the attitude altering member 31 is carried out, thereby enhancing the positioning accuracy of the tool 1 mounted to the distal end member 2.

The attitude of the distal end member 2 can be determined based on the advance or retraction position of the attitude altering member 31, which position is detected by the position detector 87. The detection value of the position detector 87—more precisely, the detection value of the linear encoder 87b—is fed back to the controller 5 for the feedback control of an output value of the attitude altering drive source 42, thereby enhancing the positioning accuracy of the tool 1.

Figure 24A:
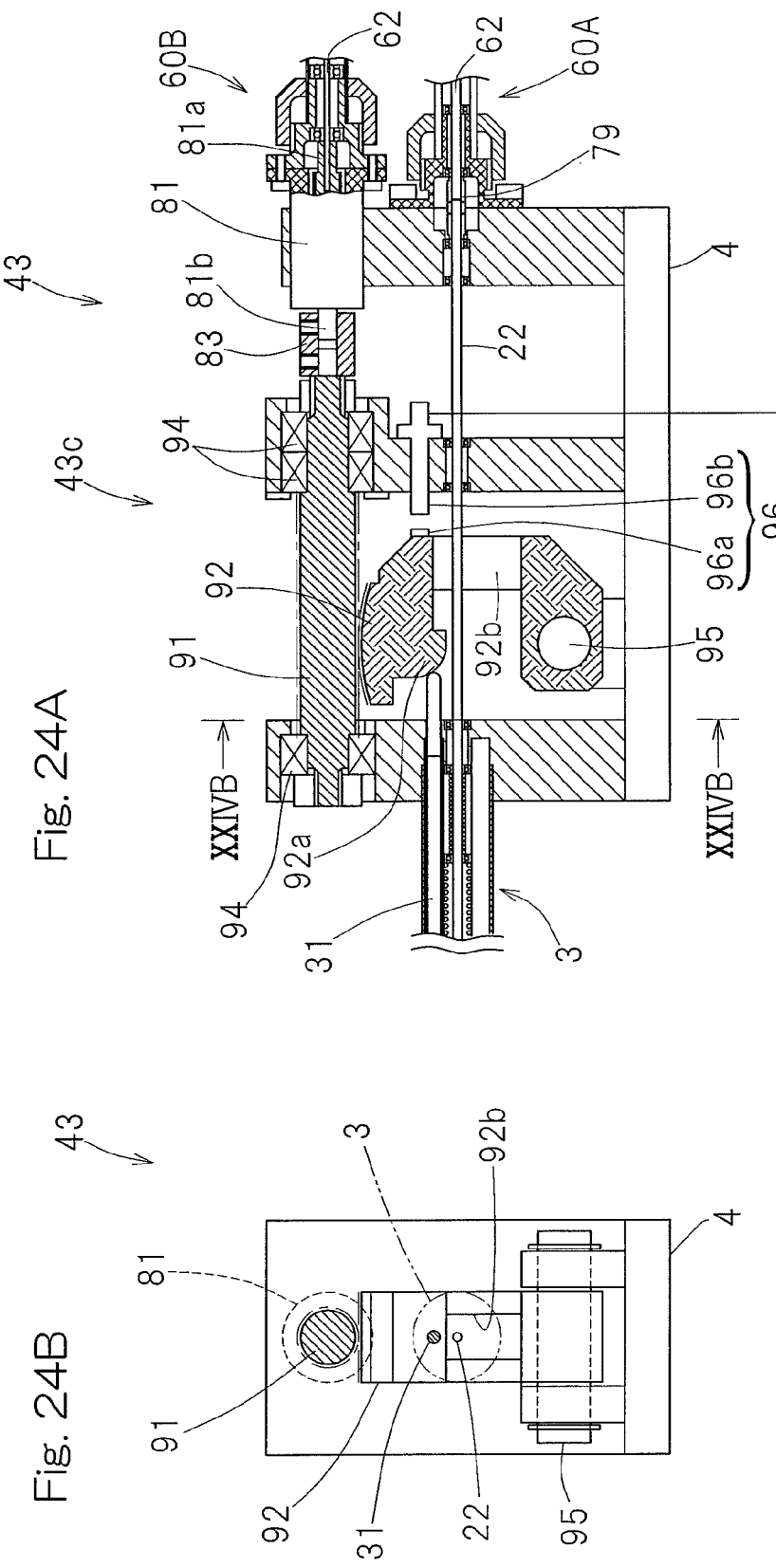
FIG. 24A is a longitudinal sectional view showing the main body base end housing having a different interior structure.
Figure 24B:
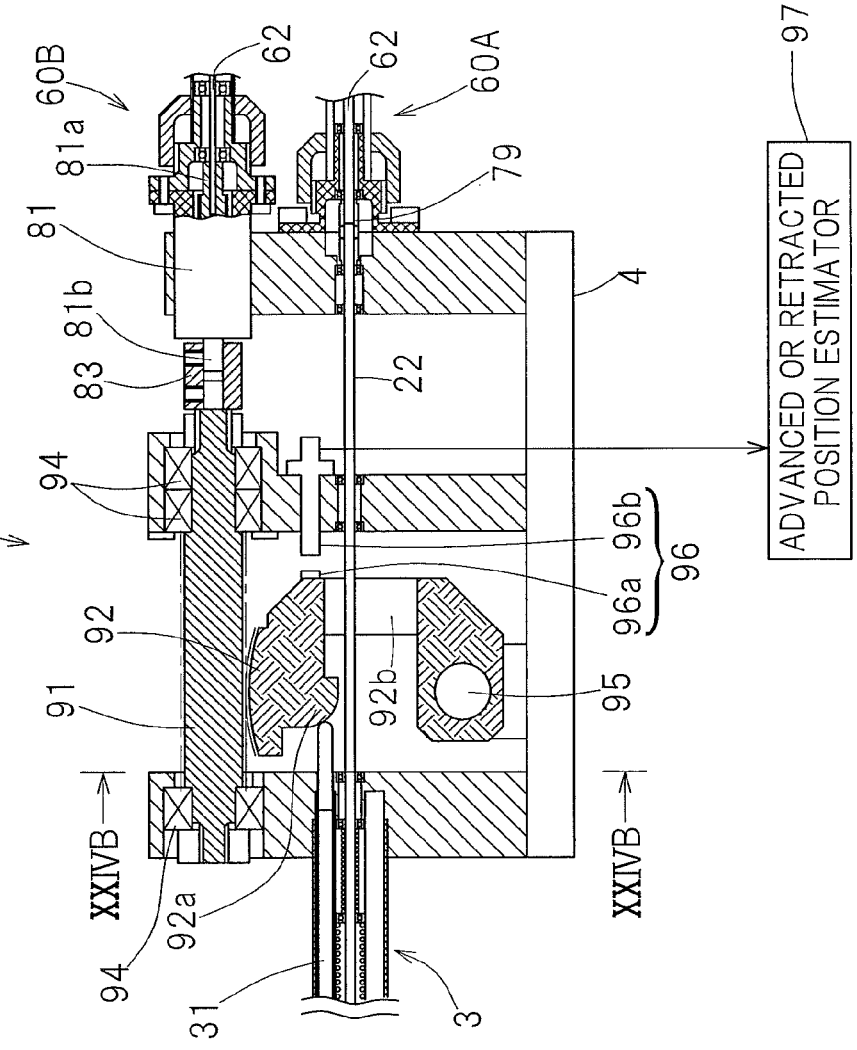
FIG. 24B is a cross sectional view taken along the line XXIVB-XXIVB in FIG. 24A.

FIGS. 24A and 24B illustrates a different example of the motion converter mechanism 43c for the attitude altering drive mechanism 43. This motion converter mechanism 43c is of a structure in which a worm 91 and a worm wheel 92 are combined together. More specifically, the motion converter mechanism 43c includes the worm 91 and the worm wheel 92 that is in mesh with the worm 91. The worm 91 has a first end and a second end opposite the first end, with the first and second ends being supported by respective bearings 94 and with the first end connecting, via the coupling 83, to the output shaft 81b of the reduction gear 81. The worm wheel 92 is supported by a support shaft 95. The worm wheel 92 forms a final output member of the motion converter mechanism, and the tip end face of the worm wheel 92 forms a contact portion 92a that contacts the base end of the attitude altering member 31. The worm wheel 92 is of a configuration having a circumference, only part of which is provided with teeth, and has an opening 92b to which the rotary shaft 22 is inserted.

Rotation of the attitude altering drive source 42 is transmitted to the reduction gear 81 via the inner wire 62 of the flexible attitude altering wire 60B and then, the speed thereof is reduced by the reduction gear 81. Further, the speed of that rotation is reduced through a reduction unit including the worm 91 and the worm wheel 92, and then is transmitted to the worm wheel 92. This results in a swing motion of the worm wheel 92 with the contact portion 92a thereof being in a sliding contact with the attitude altering member 31, to cause the attitude altering member 31 to advance or retract. Therefore, pivoting of the contact portion 92a towards the left side of FIG. 24A pushes the attitude altering member 31, causing the attitude altering member 31 to advance. On the other hand, pivoting of the contact portion 92a towards the right side of FIG. 24A results in the push-back of the attitude altering member 31 due to the elastic repulsion force of the restoring elastic member 32, causing the attitude altering member 31 to retract.

An advance or retraction position of the attitude altering member 31 is detected by a position detector 96. In the embodiment under discussion, the position detector 96 includes a detected segment 96a and a detector segment 96b that is configured to detect the displacement of the detected segment 96a. The detected segment 96a is associated with a back side (right side of FIG. 24A) of the worm wheel 92, while the detector segment 96b is fixedly provided with the main body base end housing 4. The position detector 96 may be optical or magnetic. In particular, the output of the detector segment 96b is transmitted to the advance or retraction position estimator 97 which is configured to estimate an advance or retraction position of the attitude altering member 31. In other words, the position detector 96 is operable to detect an operational position of a power transmission member—formed by the worm wheel 92—which is arranged between the reduction gear 81 and the attitude altering member 31, and the advance or retraction position estimator 97 estimates an advance or retraction position of the attitude altering member 31 from the result of the detection.

Hereinafter, an embodiment of the present invention, which make use of a different structure in the actuator main body 6 for altering the attitude of the distal end member 2 will be demonstrated.

Figures 25A, 25B:
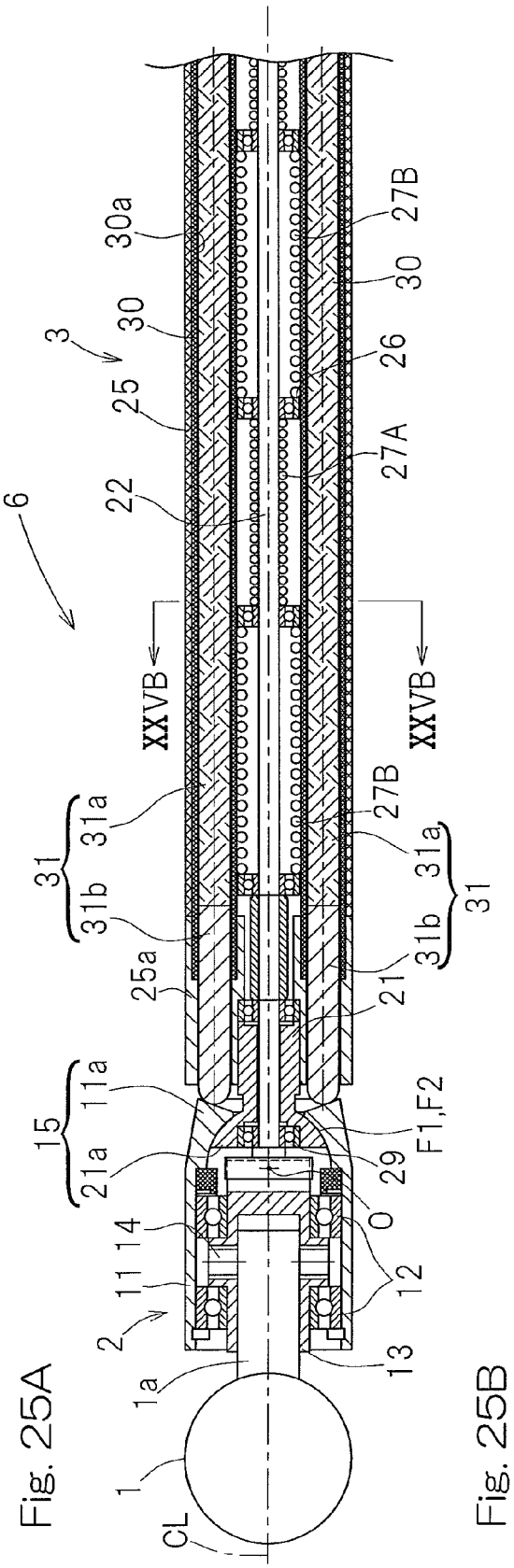
FIG. 25A is a longitudinal sectional view showing the distal end member and the spindle guide section of the remote controlled actuator assembly designed in accordance with a seventh preferred embodiment of the present invention, which assembly employs a different mechanism for altering the attitude of the distal end member.
FIG. 25B is a cross sectional view taken along the line XXVB-XXVB in FIG. 25A.

FIGS. 25A and 25B show the remote controlled actuator assembly designed in accordance with a seventh preferred embodiment of the present invention. As best shown in FIG. 25B, this actuator main body 6 includes two guide pipes 30 spaced 180 degrees in phase relative to each other within an outer shell pipe 25 and each of the guide pipes 30 has an inner diametric hole functioning as a guide hole 30a within which an attitude altering member 31 comprised of the wire 31a and the pillar shaped pins 31b in a manner similar to those described hereinbefore is inserted for advancement and retraction. Between those two guide pipes 30, a plurality of reinforcement shafts 34 are arranged on the same pitch circle diameter C as that of the guide pipes 30. As shown in FIG. 25A, no restoring elastic member 32 is provided. The guide faces F1 and F2 are spherical surfaces each having the center of curvature lying at the point O or cylindrical surfaces each having a lateral X-axis as a longitudinal axis passing through the point O.

The main body base end housing 4 (not shown) or the operating bench (not shown) is provided with two attitude altering drive sources 42 (not shown) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIG. 25A is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards as viewed in FIG. 25A.

Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 25A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by a single attitude altering member 31, the attitude stability of the distal end member 2 can be increased.

FIGS. 26A and 26B show the remote controlled actuator assembly designed in accordance with an eighth preferred embodiment of the present invention. As best shown in FIG. 26B, in the actuator main body 6 of this remote controlled actuator assembly, three guide pipes 30 are employed and arranged at respective circumferential locations spaced 120° in phase from each other within the outer shell pipe 25, and the attitude altering member 31 is reciprocally movably inserted in each of the guide holes 30a, which are inner diametric holes of such guide holes 30a, in a manner similar to that described hereinbefore. Among the three guide pipes 30, a plurality of reinforcement shafts 34 are arranged on the same pitch circle C as that of the guide pipes 30. As shown in FIG. 26A, no resilient restoring member 32 is employed. The guide faces F1 and F2 represent spherical faces having a center of curvature at a point O and the distal end member 2 can be tilted in any arbitrarily chosen direction.

The main body base end housing 4 (FIGS. 28A and 28B) or the operating bench (not shown) is provided with three attitude altering drive sources 42 (42U, 42L and 42R) for selectively advancing or retracting respective attitude altering members 31 (31U, 31L and 31R) and, accordingly, the attitude of the distal end member 2 is altered by driving those three attitude altering drive sources 42 (42U, 42L and 42R) in liaison with each other.

By way of example, when one of the attitude altering members 31U, upper side one as viewed in FIG. 26B, is advanced towards the distal, tip end side while the other two attitude altering members 31L and 31R are retracted, the housing 11 for the distal end member 2 is pressed by the upper attitude altering member 31U to allow the distal end member 2 to be altered in attitude along the guide surfaces F1 and F2 with the distal, tip end side consequently oriented downwardly as viewed in FIG. 26A. At this time, those attitude altering drive sources are controlled so that the amount of advance or retraction of each of the attitude altering members 31 may become proper. On the other hand, when each of those attitude altering members 31 is retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 26A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 26A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased. If the number of the attitude altering members 31 is increased, the attitude stability of the distal end member 2 can be yet further increased.

Figure 27A:
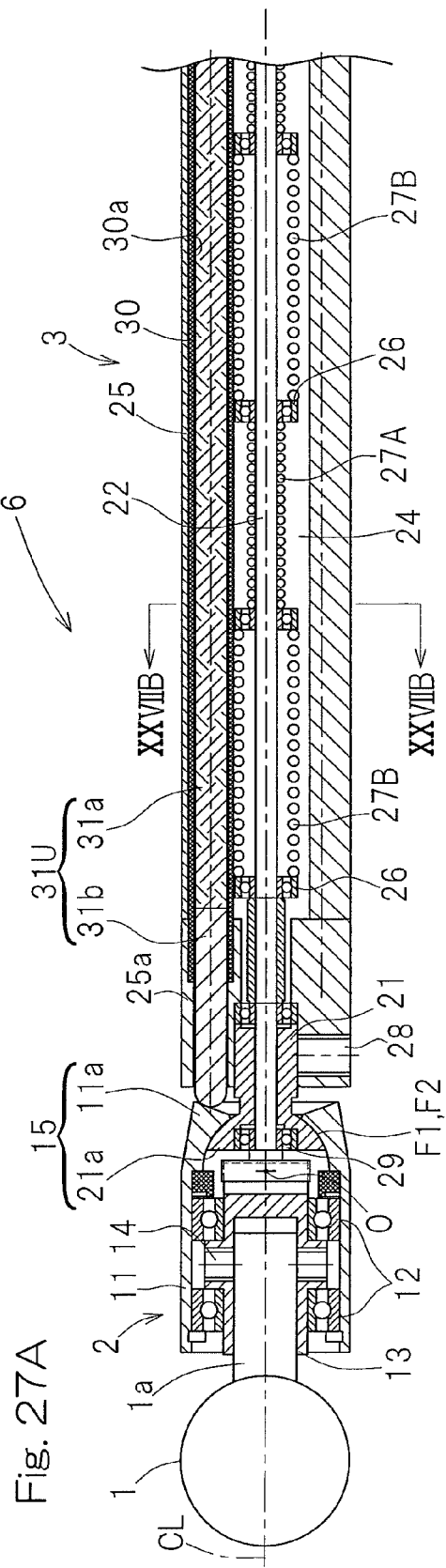
FIG. 27A is a longitudinal sectional view showing the distal end member and the spindle guide section of the remote controlled actuator assembly designed in accordance with a ninth preferred embodiment of the present invention, which assembly employs a still further different mechanism for altering the attitude of the distal end member.
Figure 27B:
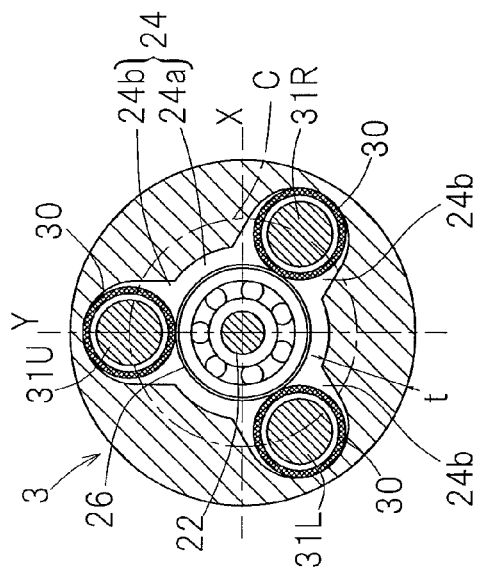
FIG. 27B is a cross sectional view taken along the line XXVIIB-XXVIIB in FIG. 27A.

FIGS. 27A and 27B illustrate a fifth preferred embodiment, in which the spindle guide section 3 has an internal structure different from the eighth embodiment shown in and described with reference to FIGS. 26A and 26B. As shown in FIG. 27B, the spindle guide section 3 employed in this actuator main body 6 is such that the outer shell pipe 25 has a hollow hole 24 made up of a round hole portion 24a at a center thereof and three grooved portions 24b formed on an outer periphery of the round hole portion 24a so as to be depressed radially outwardly from respective circumferential positions spaced 120° from each other. Each of the grooved portions 24b has a tip, a peripheral wall of which represents a semicircular shape in section. The rotary shaft 22 and the rolling bearings 26 are accommodated within the round hole portion 24a, and the guide pipe 30 is accommodated within each of grooved portions 24b.

Since the outer shell pipe 25 is made to have the above described sectional shape, the wall thickness t of portions of the outer shell pipe 25 other than the grooved portions 24b increases and as a result, the geometrical moment of inertia of the outer shell pipe 25 becomes large. In other words, the rigidity of the spindle guide section 3 is increased. Accordingly, not only can the positioning accuracy of the distal end member 2 be increased, but the cutting capability can also be increased. Also, since the guide pipes 30 are arranged within the grooved portions 24b, the positioning of the guide pipes 30 in the circumferential direction can be facilitated and as a result, the assemblability is good.

Figure 28A:
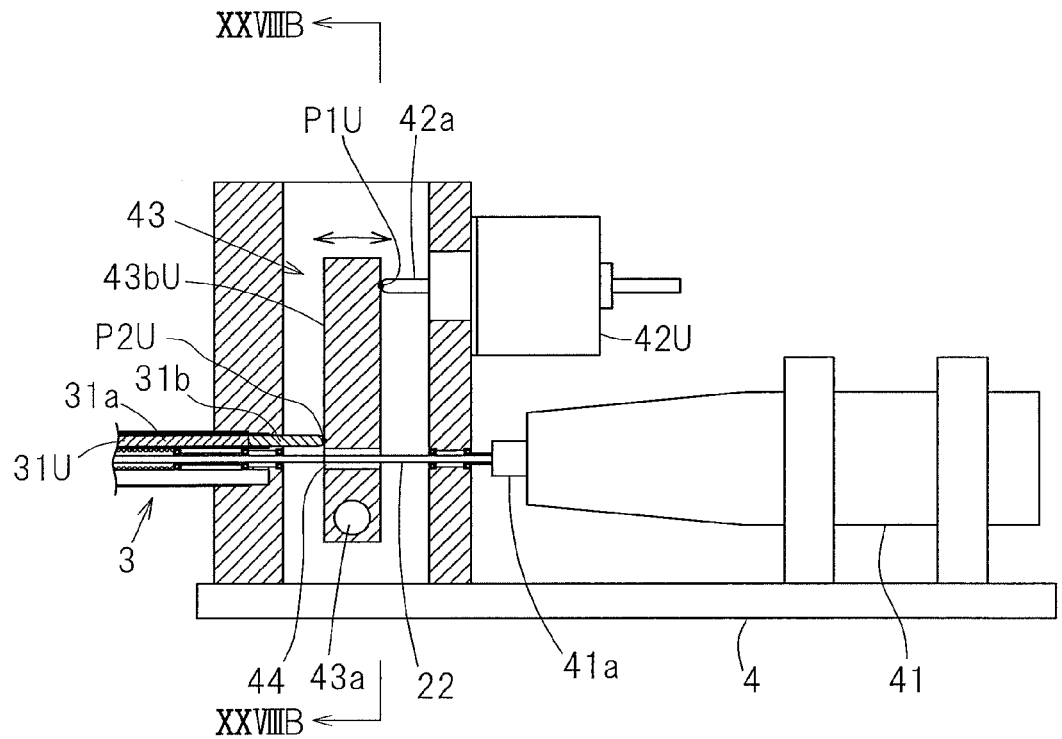
FIG. 28A is a longitudinal sectional view showing one example of the main body base end housing of the remote controlled actuator assembly shown in FIGS. 26A and 26B or FIGS. 27A and 27B.
Figure 28B:
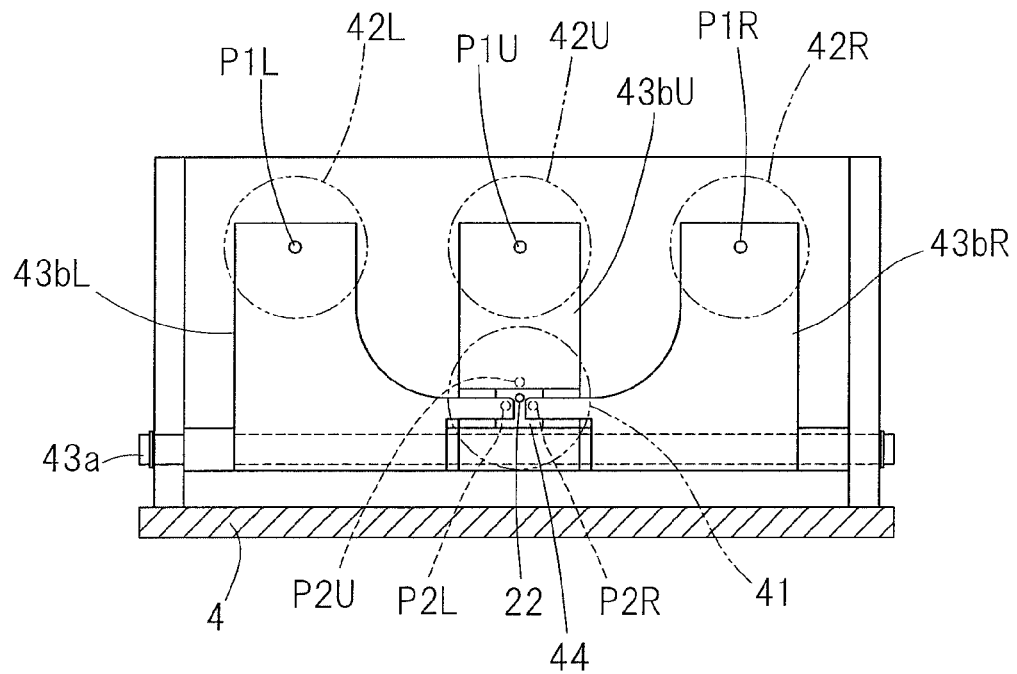
FIG. 28B is a cross sectional view taken along the line XXVIIIB-XXVIIIB in FIG. 28A.

In the actuator main body 6, in which the attitude altering member 31 is provided at the three circumferential locations as shown in FIG. 26B or FIG. 27B, the inside of the main body base end housing 4 is constructed as follows.

Where the tool rotation drive source 41 and the attitude altering drive source 42 are provided inside the main body base end housing 4, as shown in FIGS. 28A and 28B, the structure is employed in which the three attitude altering drive sources 42 (42U, 42L and 42R) for selectively advancing and retracting the respective attitude altering members 31 (31U, 31L and 31R) are disposed side by side in leftward and rightward directions and, at the same time, levers 43b (43bU, 43bL and 43bR) corresponding to the respective attitude altering drive sources 42 are rotatably provided about a common support shaft 43a. By doing so, a force of an output rod 42a of each of the attitude altering drive sources 42 acts on a working point P1 (P1U, P1L and P1R) of the associated lever 43b spaced a long distance from the support shaft 43a and a force is applied to the attitude altering member 31 at a force point P2 (P2U, P2L and P2R) spaced a short distance from the support shaft 43a. Accordingly, the output of each of the attitude altering drive sources 42 is increased and it is possible to transmit such an increased output to the corresponding attitude altering member 31. It is to be noted that the rotary shaft 22 is passed through an opening 44 defined in the lever 43bU for the upper attitude altering member 31U.

Also, where the tool rotation drive source (not shown) and the attitude altering drive source (not shown) are provided outside the main body base end housing 4, as shown in FIGS. 29A and 29B, the structure is employed in which the reduction gear 81 (81U, 81L and 81R) to which the rotation is transmitted from each of the attitude altering drive source through the flexible attitude altering wire 60B is arranged and, at the same time, three attitude altering drive mechanisms 43 (43U, 43L and 43R) for converting the rotary motion of the output shaft 81b of each of the reduction gears 81 into a linear reciprocating motion are arranged in association with the attitude altering members 31 (31U, 31L and 31R). FIGS. 29A and 29B illustrate an example in which the attitude altering drive mechanism 43 is rendered to be a motion converter mechanism of a direct acting mechanism type shown in FIGS. 23A and 23B. Each of the reduction gears 81 and each of the attitude altering drive mechanisms 43 are arranged radially about the rotary shaft 22.

Although, in describing the foregoing preferred embodiments, reference has been made to the remote controlled actuator assembly for use in the medical field, the present invention is not always limited thereto, but may be applied in various fields. For example, if the remote controlled actuator assembly of the present invention is applied to a mechanical processing, a drilling to form curved holes and cutting deep into grooves can be accomplished.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

Reference Numerals

1 . . . Tool
2 . . . Distal end member
3 . . . Spindle guide section
4 . . . Main body base end housing
6 . . . Actuator main body
15 . . . Distal end member connecting unit
22 . . . Rotary shaft
30a . . . Guide hole
31 . . . Attitude altering member
41 . . . Tool rotation drive source
42 . . . Attitude altering drive source
43 . . . Attitude altering drive mechanism
43c . . . Motion converter mechanism
50 . . . Operating bench
51 . . . Direct acting unit
52, 53 . . . Revolve pair
59, 143 . . . Freezing mechanism
60A . . . Flexible tool rotating wire
60B . . . Flexible attitude altering wire
61 . . . Outer tube
62 . . . Inner wire
63 . . . Rolling bearing
64I, 64O . . . Spring element
102A . . . Input side link actuating device
102B . . . Output side link actuating device
103 . . . Fixing trestle
104 . . . Broad fixing member
105 . . . Rotation transmitting mechanism
111A, 112A, 113A . . . Input side link mechanism
111B, 112B, 113B . . . Output side link mechanism
111a, 112a, 113a . . . End link member on fixing side
111b, 112b, 113b . . . Intermediate link member
111c, 112c, 113c . . . End link member on input or output side
114A, 114B . . . Fixing member
115A . . . Input member
115B . . . Output member
151 . . . Rotational angle detector
155 . . . Angle calculator
156 . . . Angle display unit
Q . . . Center of curvature

What is claimed is:
1. A remote controlled actuator assembly comprising:
an actuator main body having a tool at a tip end; and an operating bench of a type having an arbitrary degree of freedom, the actuator being mounted on the operating bench of a type having an arbitrary degree of freedom;

in which the actuator main body comprises a main body base end housing fixed to the operating bench, an elongated spindle guide section having a base end connected with the main body base end housing, and a distal end member fitted to a free end of the spindle guide section through a distal end member connecting unit for alteration in attitude; and in which the distal end member rotatably supports a spindle to hold the tool, the spindle guide section includes a rotary shaft to transmit a rotation of a tool rotation drive source to the spindle and a guide hole extending to opposite ends of the spindle guide section, an attitude altering member is reciprocally movably inserted within the guide hole to alter the attitude of the distal end member and is selectively advance or retract with a free end thereof held in contact with the distal end member, and an attitude altering drive mechanism is provided within the main body base end housing to selectively advance or retract the attitude altering member when driven by an attitude altering drive source.

2. The remote controlled actuator assembly as claimed in claim 1, in which the operating bench includes one or both of a revolve pair and a direct acting unit, and further comprising a freezing mechanism to freeze at least one of the revolve pair and the direct acting unit at an arbitrary position.

3. The remote controlled actuator assembly as claimed in claim 1, in which the spindle guide section has a curved portion.

4. The remote controlled actuator assembly as claimed in claim 3, in which the operating bench includes one or more revolve pairs, and in which one of those revolve pairs has the center of rotation coinciding with the center of curvature of the curved portion of the spindle guide section.

5. The remote controlled actuator assembly as claimed in claim 1, in which the operating bench comprises:

an input side link actuating device to connect an input member relative to a fixing member through three or more sets of input side link mechanisms for alteration in posture; and an output side link actuating device to connect an output member relative to a fixing member through output side link mechanisms, which are equal in number to the number of the sets of the input side link mechanism, for alteration in posture, each of the input side link mechanisms comprising: end portion link members on a fixing side and an input side each member having an one end thereof rotatably connected respectively with the fixing member and the input member; an intermediate link member to which the other ends of the respective end portion link members on the fixing side and the input side are rotatably connected; and a geometrical model, in which each of the link members is expressed by a line, representing a shape that a fixing side portion and an input side portion of the intermediate link member relative to a center portion of the intermediate link member are symmetrical with each other, each of the output side link mechanisms comprising: end portion link members on a fixing side and an output side each member having an one end thereof rotatably connected respectively with the fixing member and the output member; an intermediate link member to which the other ends of the respective end portion link members on the fixing side and the output side are rotatably connected; and a geometrical model, in which each of the link members is expressed by a line, representing a shape that a fixing side portion and an output side portion of the intermediate link member relative to a center portion of the intermediate link member are symmetrical with each other, in which two or more rotation transmitting mechanisms to transmit a rotation of the end link member on the fixing side in the input side link mechanism to the end link member on the fixing side in the output side link mechanism are provided between the two or more sets of the input side link mechanisms and the output link mechanisms out of the three or more sets of the input side link mechanisms and the output side link mechanisms, and in which the actuator main body is mounted on the output member of the output side link actuating device.

6. The remote controlled actuator assembly as claimed in claim 5, in which the input side link actuating device and the output side link actuating device are so arranged that the input side link mechanism and the output side link mechanism assume a mirror symmetry relative to each other with respect to the fixing member.

7. The remote controlled actuator assembly as claimed in claim 5, in which the input side link actuating device and the output side link actuating device are so arranged that the input side link mechanism and the output side link mechanism assume a rotational symmetry relative to each other with respect to the fixing member.

8. The remote controlled actuator assembly as claimed in claim 5, further comprising a rotational angle detector provided in two or more sets of the input side link mechanisms or the output side link mechanisms to detect the angle of rotation of the end link member on the fixing side.

9. The remote controlled actuator assembly as claimed in claim 8, further comprising:

an angle calculator to calculate the angle of the output member by means of a forward transform of an output signal of the rotational angle detector, and an angle display unit to display the angle of the output member calculated by the angle calculator.

10. The remote controlled actuator assembly as claimed in claim 5, in which one or both of the tool rotation drive source and the attitude altering drive source is/are provided in the fixing member, and in which one or both of a flexible tool rotating wire to transmit a rotation of the tool rotation drive source to the rotary shaft and a flexible attitude altering wire to transmit a rotation of the attitude altering drive source to the attitude altering drive mechanism is/are provided having been inserted inside the output side link mechanism of the output side link actuating device.

11. The remote controlled actuator assembly as claimed in claim 10, in which each of the flexible tool rotating wire and the flexible attitude altering wire is of a structure in which within the interior of an outer tube having a flexibility, a flexible inner wire having opposite ends serving respectively as input and output ends of rotation is rotatably supported by a plurality of rolling bearings, and spring elements to apply preloads to the rolling bearings are interposed between the neighboring rolling bearings.

12. The remote controlled actuator assembly as claimed in claim 5, in which the attitude altering drive source is provided in the fixing member, and a rotation of this attitude altering drive source is transmitted to an input shaft of the attitude altering drive mechanism through a flexible attitude altering wire, and in which the attitude altering drive mechanism includes an motion converter mechanism to convert a rotation of the input shaft into an advancing and retracting motion, and a center axis of a rotatable portion of the motion converter mechanism is arranged parallel to the input shaft and the rotary shaft at the base end of the spindle guide.

13. The remote controlled actuator assembly as claimed in claim 12, in which each of the flexible tool rotating wire and the flexible attitude altering wire is of a structure in which within the interior of an outer tube having a flexibility, a flexible inner wire having opposite ends serving respectively as input and output ends of rotation is rotatably supported by a plurality of rolling bearings, and spring elements to apply preloads to the rolling bearings are interposed between the neighboring rolling bearings.

\* \* \* \* \*